(12) United States Patent
Ortyn et al.

(10) Patent No.: US 8,660,332 B2
(45) Date of Patent: Feb. 25, 2014

(54) BLOOD AND CELL ANALYSIS USING AN IMAGING FLOW CYTOMETER

(71) Applicant: Amnis Corporation, Seattle, WA (US)

(72) Inventors: William E. Ortyn, Bainbridge Island, WA (US); David A. Basiji, Seattle, WA (US); Philip J. Morrissey, Bellevue, WA (US); Thaddeus C. George, Seattle, WA (US); Brian E. Hall, Seattle, WA (US); Cathleen A. Zimmerman, Bainbridge Island, WA (US); David J. Perry, Woodinville, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 13/798,442

(22) Filed: Mar. 13, 2013

(65) Prior Publication Data
US 2013/0201317 A1      Aug. 8, 2013

Related U.S. Application Data

(60) Division of application No. 12/631,795, filed on Dec. 4, 2009, now Pat. No. 8,406,498, which is a continuation-in-part of application No. 12/362,170,
(Continued)

(51) Int. Cl.
*G06K 9/00* (2006.01)

(52) U.S. Cl.
USPC .......................................... 382/133; 356/326

(58) Field of Classification Search
USPC ............ 382/128, 133, 134, 321; 356/39, 326, 356/328, 417, 418, 419; 359/633, 634
See application file for complete search history.

(56) References Cited

U.S. PATENT DOCUMENTS

| 3,497,690 A | 2/1970 | Wheeles, Jr. et al. ............ 250/71 |
| 3,555,280 A | 1/1971 | Richards, Jr. ................. 250/201 |

(Continued)

FOREIGN PATENT DOCUMENTS

| EP | 0154404 B1 | 6/1991 | .............. G06F 15/68 |
| EP | 0281327 B1 | 6/1993 | ........... G01N 33/546 |

(Continued)

OTHER PUBLICATIONS

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." Cytometry: 48:194-201.

(Continued)

*Primary Examiner* — Andrew W Johns
(74) *Attorney, Agent, or Firm* — Lee & Hayes, PLLC

(57) ABSTRACT

Multimodal or multispectral images of cells comprising a population of cells are simultaneously collected. Photometric and/or morphometric image features identifiable in the images are used to identify differences between first and second populations of cells. The differences can include changes in a relative percentage of different cell types in each population, or a change in a first type of cell present in the first population of cells and the same type of cell in the second population of cells. The changes may be indicative of a disease state, indicative of a relative effectiveness of a therapy, or indicative of a health of the person from whom the cells populations were obtained.

19 Claims, 15 Drawing Sheets

Related U.S. Application Data filed on Jan. 29, 2009, now Pat. No. 7,634,126, which is a division of application No. 11/344,941, filed on Feb. 1, 2006, now Pat. No. 7,522,758, and a continuation-in-part of application No. 11/123,610, filed on May 4, 2005, now Pat. No. 7,450,229, and a continuation-in-part of application No. 10/628,662, filed on Jul. 28, 2003, now Pat. No. 6,975,400, which is a continuation-in-part of application No. 09/976,257, filed on Oct. 12, 2001, now Pat. No. 6,608,682, which is a continuation-in-part of application No. 09/820,434, filed on Mar. 29, 2001, now Pat. No. 6,473,176, which is a continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341.

(60) Provisional application No. 60/649,373, filed on Feb. 1, 2005, provisional application No. 60/567,911, filed on May 4, 2004, provisional application No. 60/117,203, filed on Jan. 25, 1999, provisional application No. 60/240,125, filed on Oct. 12, 2000.

(56) References Cited

U.S. PATENT DOCUMENTS

| | | | | |
|---|---|---|---|---|
| 3,586,760 | A | 6/1971 | Dillenburger | 178/5.4 |
| 3,922,069 | A | 11/1975 | Kishikawa et al. | 355/173 |
| 4,313,734 | A | 2/1982 | Leuvering | 23/23 |
| 4,414,575 | A | 11/1983 | Yamamoto et al. | 358/227 |
| 4,635,293 | A | 1/1987 | Watanabe | 382/44 |
| 4,662,742 | A | 5/1987 | Chupp | 356/39 |
| 4,677,680 | A | 6/1987 | Harima et al. | 382/1 |
| 4,703,017 | A | 10/1987 | Campbell et al. | 436/501 |
| 4,737,932 | A | 4/1988 | Baba | 364/900 |
| 4,770,992 | A | 9/1988 | Van den Engh et al. | 435/6 |
| 4,777,525 | A | 10/1988 | Preston, Jr. | 358/102 |
| 4,786,165 | A | 11/1988 | Yamamoto et al. | 356/23 |
| 4,845,197 | A | 7/1989 | Petersen et al. | 530/387 |
| 4,857,453 | A | 8/1989 | Ullman et al. | 435/7 |
| 5,096,807 | A | 3/1992 | Leaback | 435/6 |
| 5,107,522 | A | 4/1992 | Kitayama et al. | 375/97 |
| 5,122,453 | A | 6/1992 | Martin et al. | 435/7.24 |
| 5,141,609 | A | 8/1992 | Sweedler et al. | 204/180.1 |
| 5,153,916 | A | 10/1992 | Inagaki et al. | 382/4 |
| 5,159,397 | A | 10/1992 | Kosaka et al. | 356/73 |
| 5,159,398 | A | 10/1992 | Maekawa et al. | 356/73 |
| 5,159,642 | A | 10/1992 | Kosaka | 382/6 |
| 5,247,339 | A | 9/1993 | Ogino | 356/73 |
| 5,247,340 | A | 9/1993 | Ogino | 356/73 |
| 5,257,182 | A | 10/1993 | Luck et al. | 364/413.1 |
| 5,272,354 | A | 12/1993 | Kosaka | 250/574 |
| 5,351,311 | A | 9/1994 | Rogers et al. | 382/45 |
| 5,372,936 | A | 12/1994 | Fraatz et al. | 435/34 |
| 5,422,712 | A | 6/1995 | Ogino | 356/73 |
| 5,436,144 | A | 7/1995 | Stewart et al. | 435/91.2 |
| 5,444,527 | A | 8/1995 | Kosaka | 356/73 |
| 5,459,240 | A | 10/1995 | Foxwell et al. | 530/328 |
| 5,471,294 | A | 11/1995 | Ogino | 356/73 |
| 5,547,849 | A | 8/1996 | Baer et al. | 435/7.24 |
| 5,548,349 | A | 8/1996 | Mizuguchi et al. | 348/766 |
| 5,548,395 | A | 8/1996 | Kosaka | 356/73 |
| 5,568,315 | A | 10/1996 | Shuman | 359/487 |
| 5,596,401 | A | 1/1997 | Kusuzawa | 356/23 |
| 5,621,460 | A | 4/1997 | Hatlestad et al. | 348/265 |
| 5,625,048 | A | 4/1997 | Tsien et al. | 536/23.4 |
| 5,633,503 | A | 5/1997 | Kosaka | 250/458.1 |
| 5,644,388 | A | 7/1997 | Maekawa et al. | 356/73 |
| 5,674,743 | A | 10/1997 | Ulmer | 435/287.2 |
| 5,686,960 | A | 11/1997 | Sussman et al. | 343/213 |
| 5,695,934 | A | 12/1997 | Brenner | 435/6 |
| 5,733,721 | A | 3/1998 | Hemstreet, III et al. | 435/6 |
| 5,754,291 | A | 5/1998 | Kain | 356/338 |
| 5,760,899 | A | 6/1998 | Eismann | 356/326 |
| 5,764,792 | A | 6/1998 | Kennealy | 382/133 |
| 5,784,162 | A | 7/1998 | Cabib et al. | 356/346 |
| RE35,868 | E | 8/1998 | Kosaka | 250/574 |
| 5,828,776 | A | 10/1998 | Lee et al. | 382/133 |
| 5,831,723 | A | 11/1998 | Kubota et al. | 356/73 |
| 5,844,670 | A | 12/1998 | Morita et al. | 356/124 |
| 5,848,123 | A | 12/1998 | Strommer | 378/98.8 |
| 5,855,753 | A | 1/1999 | Trau et al. | 204/484 |
| 5,900,942 | A | 5/1999 | Spiering | 356/400 |
| 5,926,283 | A | 7/1999 | Hopkins | 356/419 |
| 5,929,986 | A | 7/1999 | Slater et al. | 356/326 |
| 5,959,953 | A | 9/1999 | Alon | 369/44.41 |
| 5,985,549 | A | 11/1999 | Singer et al. | 435/6 |
| 5,986,061 | A | 11/1999 | Pestka | |
| 6,007,994 | A | 12/1999 | Ward et al. | 435/6 |
| 6,007,996 | A | 12/1999 | McNamara et al. | 435/6 |
| 6,014,468 | A | 1/2000 | McCarthy et al. | 382/254 |
| 6,066,459 | A | 5/2000 | Garini et al. | 435/6 |
| 6,108,082 | A | 8/2000 | Pettipiece et al. | 356/301 |
| 6,115,119 | A | 9/2000 | Sieracki et al. | 356/337 |
| 6,116,739 | A | 9/2000 | Ishihara et al. | 353/31 |
| 6,156,465 | A | 12/2000 | Cao et al. | 430/30 |
| 6,159,686 | A | 12/2000 | Kardos et al. | 435/6 |
| 6,210,973 | B1 | 4/2001 | Pettit | 436/172 |
| 6,211,955 | B1 | 4/2001 | Basiji et al. | 356/326 |
| 6,229,913 | B1 | 5/2001 | Nayar et al. | 382/154 |
| 6,249,314 | B1 | 6/2001 | Yamamoto et al. | 348/242 |
| 6,249,341 | B1 | 6/2001 | Basiji et al. | 356/73 |
| 6,256,096 | B1 | 7/2001 | Johnson | 356/335 |
| 6,259,807 | B1 | 7/2001 | Ravkin | 382/133 |
| 6,330,081 | B1 | 12/2001 | Scholten | 358/463 |
| 6,330,361 | B1 | 12/2001 | Mitchell et al. | 382/211 |
| 6,381,363 | B1 | 4/2002 | Murching et al. | 382/164 |
| 6,473,176 | B2 | 10/2002 | Basiji et al. | 356/326 |
| 6,507,391 | B2 | 1/2003 | Riley et al. | 56/28 |
| 6,510,319 | B2 | 1/2003 | Baum et al. | 455/442 |
| 6,519,355 | B2 | 2/2003 | Nelson | 382/133 |
| 6,522,781 | B1 | 2/2003 | Norikane et al. | 382/203 |
| 6,532,061 | B2 | 3/2003 | Ortyn et al. | 356/28 |
| 6,548,259 | B2 | 4/2003 | Ward et al. | 435/6 |
| 6,549,664 | B1 | 4/2003 | Daiber et al. | 382/232 |
| 6,563,583 | B2 | 5/2003 | Ortyn et al. | 356/400 |
| 6,580,504 | B1 | 6/2003 | Ortyn et al. | 356/338 |
| 6,583,865 | B2 | 6/2003 | Basiji et al. | 356/73 |
| 6,608,680 | B2 | 8/2003 | Basiji et al. | 356/338 |
| 6,608,682 | B2 | 8/2003 | Ortyn et al. | 356/419 |
| 6,618,140 | B2 | 9/2003 | Frost et al. | 356/317 |
| 6,620,591 | B1 | 9/2003 | Dunlay et al. | 435/7.2 |
| 6,658,143 | B2 | 12/2003 | Hansen et al. | 382/133 |
| 6,671,044 | B2 | 12/2003 | Ortyn et al. | 356/326 |
| 6,671,624 | B1 | 12/2003 | Dunlay et al. | 702/19 |
| 6,707,551 | B2 | 3/2004 | Ortyn et al. | 356/338 |
| 6,716,588 | B2 | 4/2004 | Sammak et al. | 435/7.23 |
| 6,727,066 | B2 | 4/2004 | Kaser | 435/6 |
| 6,763,149 | B2 | 7/2004 | Riley et al. | 382/294 |
| 6,778,263 | B2 | 8/2004 | Ortyn et al. | 356/28 |
| 6,873,733 | B2 | 3/2005 | Dowski, Jr. | 382/232 |
| 6,875,973 | B2 | 4/2005 | Ortyn et al. | 250/201.3 |
| 6,906,792 | B2 | 6/2005 | Ortyn et al. | 356/28.5 |
| 6,927,922 | B2 | 8/2005 | George et al. | 359/708 |
| 6,934,408 | B2 | 8/2005 | Frost et al. | 382/129 |
| 6,947,128 | B2 | 9/2005 | Basiji et al. | 356/73 |
| 6,947,136 | B2 | 9/2005 | Ortyn et al. | 356/338 |
| 6,975,400 | B2 | 12/2005 | Ortyn et al. | 356/419 |
| 7,006,710 | B2 | 2/2006 | Riley et al. | 382/294 |
| 7,033,819 | B2 | 4/2006 | Kim et al. | 435/286.2 |
| 7,042,639 | B1 | 5/2006 | McDowell | 359/398 |
| 7,050,620 | B2 | 5/2006 | Heckman | 382/133 |
| 7,057,732 | B2 | 6/2006 | Jorgenson et al. | 356/445 |
| 7,079,708 | B2 | 7/2006 | Riley et al. | 382/294 |
| 7,087,877 | B2 | 8/2006 | Ortyn et al. | 250/201.2 |
| 7,139,415 | B2 | 11/2006 | Finkbeiner | 382/128 |
| 7,180,673 | B2 | 2/2007 | Dowski, Jr. | 359/637 |
| 7,190,832 | B2 | 3/2007 | Frost et al. | 382/173 |
| 7,221,457 | B2 | 5/2007 | Jorgenson et al. | 356/445 |
| 7,289,205 | B2 | 10/2007 | Yaroslavsky et al. | 356/317 |
| 7,315,357 | B2 | 1/2008 | Ortyn et al. | 356/73 |

(56) References Cited

U.S. PATENT DOCUMENTS

| | | | |
|---|---|---|---|
| 7,450,229 B2 | 11/2008 | Ortyn et al. | 356/326 |
| 7,522,758 B2 | 4/2009 | Ortyn et al. | 382/133 |
| 7,567,695 B2 | 7/2009 | Frost et al. | 382/129 |
| 7,667,761 B2 | 2/2010 | Thomas | 348/335 |
| 7,925,069 B2 * | 4/2011 | Ortyn et al. | 382/133 |
| 8,131,053 B2 | 3/2012 | Ortyn et al. | 382/133 |
| 2001/0006416 A1 | 7/2001 | Johnson | 356/73 |
| 2001/0012620 A1 | 8/2001 | Rich | 435/7.1 |
| 2002/0126275 A1 | 9/2002 | Johnson | 356/317 |
| 2002/0146734 A1 | 10/2002 | Ortyn et al. | 435/6 |
| 2003/0048931 A1 | 3/2003 | Johnson et al. | 382/128 |
| 2003/0049701 A1 | 3/2003 | Muraca | 435/7.23 |
| 2003/0059093 A1 | 3/2003 | Rosania et al. | 382/128 |
| 2003/0104439 A1 | 6/2003 | Finch | 435/6 |
| 2004/0093166 A1 | 5/2004 | Kil | 702/19 |
| 2004/0111220 A1 | 6/2004 | Ochs et al. | 702/19 |
| 2004/0241759 A1 | 12/2004 | Tozer et al. | 435/7.2 |
| 2005/0014129 A1 | 1/2005 | Cliffel et al. | 435/4 |
| 2006/0246481 A1 | 11/2006 | Finch et al. | 435/6 |
| 2006/0257884 A1 | 11/2006 | Brawley et al. | 435/6 |
| 2007/0054350 A1 | 3/2007 | Walker | 435/34 |
| 2008/0240539 A1 | 10/2008 | George et al. | 382/133 |
| 2009/0202130 A1 | 8/2009 | George et al. | 382/133 |
| 2010/0232675 A1 | 9/2010 | Ortyn et al. | 382/134 |

FOREIGN PATENT DOCUMENTS

| | | | |
|---|---|---|---|
| EP | 0280559 B1 | 10/1993 | G01N 33/546 |
| EP | 0372707 B1 | 3/1996 | C07K 14/00 |
| EP | 0950890 A2 | 10/1999 | G01N 15/14 |
| EP | 1316793 A1 | 6/2003 | G01N 21/47 |
| JP | 62134559 A | 6/1987 | G01N 33/49 |
| JP | 2004522163 A | 7/2004 | G01N 21/17 |
| WO | WO8808534 A1 | 11/1988 | G01N 33/543 |
| WO | WO9010715 A1 | 9/1990 | C12Q 1/68 |
| WO | WO9520148 A1 | 7/1995 | G01N 21/64 |
| WO | WO9726333 A1 | 7/1997 | C12N 15/12 |
| WO | WO9853093 A1 | 11/1998 | C12Q 1/00 |
| WO | WO9853300 A2 | 11/1998 | G01N 21/00 |
| WO | WO9924458 A1 | 5/1999 | C07K 1/10 |
| WO | WO9964592 A2 | 12/1999 | C12N 15/12 |
| WO | WO0006989 A2 | 2/2000 | |
| WO | WO0014545 A1 | 3/2000 | G01N 33/58 |
| WO | WO0042412 A1 | 7/2000 | G01N 15/02 |
| WO | WO0111341 A2 | 2/2001 | G01N 15/14 |
| WO | WO0146675 A2 | 6/2001 | G01N 15/14 |
| WO | WO0217622 A1 | 2/2002 | H04N 5/232 |
| WO | WO0218537 A2 | 3/2002 | |
| WO | WO0231182 A2 | 4/2002 | |
| WO | WO0235474 A1 | 5/2002 | G06T 7/00 |
| WO | WO02073200 A1 | 9/2002 | G01N 33/53 |
| WO | WO02079391 A2 | 10/2002 | |
| WO | WO2005090945 A1 | 9/2005 | G01N 15/14 |
| WO | WO2005098430 A2 | 10/2005 | G01N 33/50 |

OTHER PUBLICATIONS

Schmid et al., "Evaluation of inter-scorer and inter-laboratory reliability of the mouse epididymal sperm aneuploidy (m-ESA) assay," Mutagenesis vol. 16, No. 3: 189-195, 2001.

Schmid et al., "Simultaneous Flow Cytometric Analysis of Two Cell Surface Markers, Telomere Length, and DNA Content," Cytometry 49: 96-105, 2002.

Schwerin et al., "Quantification of Y Chromosome Bearing Spermatozoa of Cattle Using In Situ Hybridization," Molecular Reproduction and Development 30: 39-43, 1991.

Shi et al., "Aneuploidy in human sperm: a review of the frequency and distribution of aneuploidy, effects of donor age and lifestyle factors," Cytogenetics and Cell Genetics 90: 219-226, 2000.

Timm et al., "Amplification and Detection of a Y-Chromosome DNA Sequence by Fluorescence In Situ Polymerase Chain Reaction and Flow Cytometry Using Cells in Suspension," Cytometry (Communications in Clinical Cytometry) 22: 250-255, 1995.

Timm et al., "Fluorescent In Situ Hybridization En Suspension (FISHES) Using Digoxigenin-qLabeled Probes and Flow Cytometry," Biotechniques vol. 12, No. 3: 362-367, 1992.

Trask et al., "Fluorescence in situ hybridization to interphase cell nuclei in suspension allows flow cytometric analysis of chromosome content and microscopic analysis of nuclear organization," Human Genetics 78:251-259, 1988.

Tucker et al., "Extended depth of field and aberration control for inexpensive digital microscope systems" Optics Express vol. 4, No. 11:467-474, May 24, 1999.

van Dekken et al., "Flow Cytometric Quantification of Human Chromosome Specific Repetitive DNA Sequences by Single and Bicolor Fluorescent In Situ Hybridization to Lymphocyte Interphase Nuclei," Cytometry 11: 153-164, 1990.

van den Berg et al., "Detection of Y Chromosome by In situ Hybridization in Combination with Membrane Antigens by Two-Color Immunofluorescence," Laboratory Investigation vol. 64, No. 5: 623-628, 1991.

Wang, Fu-sheng and Fumio Kubota. 2002. "A Novel Apoptosis Research Method With Imaging-Combined Flow Cytometer and HITC or IR-125 Staining." Cytometry: 50:267-274.

Weber-Matthieson et al., "Rapid immunophenotypic characterization of chromosomally aberrant cells by the new FICTION method," Cytogenetics Cell Genetics 63: 123-125, 1993.

Weber-Matthieson et al., "Simultaneous Fluorescence Immunophenotyping and Interphase Cytogenetics: A Contribution to the Characterization of Tumor Cells," Journal of Histochemistry and Cytochemistry vol. 40, No. 2:171-175, 1992.

Wietzorrek, Joachim et al. 1999. "A New Multiparameter Flow Cytometer: Optical and Electrical Cell Analysis in Combination With Video Microscopy in Flow." Cytometry: 35:291-301.

Wyrobek et al., "Detection of Sex Chromosomal Aneuploidies X—X, Y—Y, and X—Y, in Human Sperm Using Two-Chromosome Fluorescence In Situ Hybridization," American Journal of Medical Genetics 53: 1-7, 1994.

Wyrobek et al., "Fluorescence In Situ Hybridization to Y Chromosomes in Decondensed Human Sperm Nuclei," Molecular Reproduction and Development 27: 200-208, 1990.

Wyrobek et al., "Smokers produce more aneuploid sperm than non-smokers," The American Society of Human Genetics, 45th Annual Meeting, A131: 737, Oct. 24-28, 1995.

Amman et al., "Fluorescent-Oligonucleotide Probing of Whole Cells for Determinative, Phylogenetic, and Environmental Studies in Microbiology," Journal of Bacteriology vol. 172, No. 2: 762-770, Feb. 1990.

Arkesteijn et al. "Chromosome Specific DNA Hybridization in Suspension for Flow Cytometric Detection of Chimerism in Bone Marro Transplantation and Leukemia," Cytometry 19: 353-360, Apr. 1995.

Baines et al., "Flow Cytometric Quantitation of Sequence-Specific mRNA in Hemopoietic Cell Suspension by Primer-Induced in Situ (PRINS) Fluorescent Nucleotide Labeling," Experimental Cell Research 208: 321-326, Sep. 1993.

Barren III et al., "Method for Identifying Prostate Cells in Semen Using Flow Cytometry," The Prostate 36: 181-188, Aug. 1998.

Bauman et al., "Flow Cytometric Detection of Ribosomal RNA in Suspended Cells by Fluorescent In Situ Hybridization," Cytometry 9: 517-524, Nov. 1998.

Baumgartner et al., "Automated Evaluation of Frequencies of Aneuploid Sperm by Laser-Scanning Cytometry (LSC)," Cytometry 44: 156-160, Jun. 2001.

Ben-Eliezer et al., "All-optical extended depth of field imaging system," Journal of Optics A: Pure and Applied Optics 5: SI64-S169, Sep. 2003.

Biggs et al., "Acceleration of iterative image restoration algorithms" Applied Optics vol. 36, No. 8: 1766-1775, Mar. 10, 1997.

Boyle et al., "Isolation and Initial Characterization of a Large Repeat Sequence Element Specific to Mouse Chromosome 8," Genomics vol. 12, No. 3: 517-525, Mar. 1992.

Callet-Bauchu et al., "Distribution of the cytogenetic abnormality +i(3)(q10) in persistent polyclonal B-cell lymphocytosis: a FICTION study in three cases," British Journal of Haematology 99: 531-536, Dec. 1997.

(56) References Cited

OTHER PUBLICATIONS

Ding et al., "Characterization and Quantitation of NF-KB Nuclear Translocation Induced by Interleukin-1 and Tumor Necrosis Factor-u," The Journal of Biological Chemistry vol. 273, No. 44: 28897-28905, Oct. 30, 1998.
Disteche et al., "Isolation and characterization of two repetitive DNA fragments located near the centromere of the mouse X chromosome," Cytogenetics and Cell Genetics 39: 262-268, 1985.
Dragowska et al., "Measurement of DNA repeat sequence by flow cytometry," Cytometry Supplement 7: 51, Oct. 1994.
Engvall, Eva. "Enzyme Immunoassay ELISA and EMIT," Methods in Enzymology vol. 70, Part A: 419-439, Dec. 1980.
Femandez-Lago et al., "Fluorescent Whole-Cell Hybridization with 16S rRNA-Targeted Oligonucleotide Probes to Identify Brucella spp. By Flow Cytometry," Journal of Clinical Microbiology vol. 38, No. 7: 2768-2771, Jul. 2000.
Ferraro et al., "Extended focused image in microscopy by digital holography," Optics Express, vol. 13, No. 18: 6738-6749, Sep. 2005.
George, Thaddeus, David A. Basiji, Brian E. Hall, David H. Lynch, William E. Ortyn, David J. Perry, Michael J. Seo, Cathleen A. Zimmerman, and Philip J. Morrissey. "Distinguishing Modes of Cell Death Using the ImageStream Multispectral Imaging Flow Cytometer" Cytometry Part A 59A:237-245, Jun. 2004.
George et al., "Extended depth of field using a logarithmic asphere" Journal of Optics A: Pure and Applied Optics 5: SI57-S163, Sep. 2003.
George, Thaddeus C., Stacey L. Fanning, Patricia Fitzgeral-Bocarsly, Ricardo B. Medeiros, Sarah Highfill, Yoji Shimizu, Brian E. Hall, Keith Frost, David Basiji, William E. Ortyn, Philip J. Morrissey, David H. Lynch. "Quantitative measurement of nuclear translocation events using similarity analysis of multispectral cellular images obtained in flow," Journal of Immunological Methods, 311, Apr. 2006, 117-129.
Gordy, Claire et al., "Visualization of antigen presentation by actin-mediated targeting of glycolipid-enriched membrane domains to the immune synapse of B cell APCs." Journal of Immunology, vol. 172, No. 4, Feb. 15, 2004. pp. 2030-2038, XP002481372 ISSN: 0022-1767.
Hecht, Eugene. "Optics 4th ed." 2002. Addison-Wesley Longman, Inc., XP-002465391. ISBN: 0-8053-8566-5.
Hultdin et al., "Telomere analysis by fluorescence in situ hybridization and flow cytometry," Nucleic Acids Research vol. 26, No. 16: 3651-3656, Aug. 15, 1998.
Kubota, F., "Analysis of red cell and platelet morphology using an imaging-combined flow cytometer." Clin. Lab. Haem., Apr. 2003, 25:71-76.
Kubota, Fumio et al., "Flow Cytometer and Imaging Device Used in Combination." Cytometry, Oct. 1995, 21:129-132.
Lauzon et al., "Flow Cytometric Measurement of Telomere Length," Cytometry 42: 159-164, Jun. 2000.
Levron et al., "Sperm chromosome abnormalities in men with severe male factor infertility who are undergoing in vitro fertilization with intracytoplasmic sperm injection," Fertility and Sterility vol. 76, No. 3: 479-484, Sep. 2001.
Lowe et al., "Aneuploid epididymal sperm detected in chromosomally normal and Robertsonian translocation-bearing mice using a new three-chromosome Fish method," Chromosoma 105: 204-210, 1996.
Majno et al., "Apoptosis, Oncosis, and Necrosis, An Overview of Cell Death," American Journal of Pathology vol. 146, No. 1: 3-15, Jan. 1, 1995.
Martin et al., "Detection of aneuploidy in human interphase spermatozoa by fluorescence in situ hybridization (FISH)," Cytogenetics and Cell Genetics 64: 23-26, 1993.
Nautiyal et al., "17B-Estradiol induces nuclear translocation of CrkL at the window of embryo implantation," Biochemical and Biophysical Research Communications 318: 103-112, 2004.
Non-Final Office Action for U.S. Appl. No. 12/631,795, mailed on Aug. 14, 2012, William Ortyn et al., "Blood and Cell Analysis Using an Imaging Flow Cytometer", 9 pages.

Oberholzer et al., "Methods in quantitative image analysis," Histochem Cell Biol, vol. 105: 333-355, May 1996.
Ong, S.H. and P.M. Nickolls, "Analysis of MTF Degradation in the Imaging of Cells in a Flow System." International Journal of Imaging Systems & Technology, Autum(Fall) 1994, 5:243-250.
Ong, Sim Hen, "Development of a System for Imaging and Classifying Biological Cells in a Flow Cytometer," Doctor of Philosophy Thesis. University of Sydney, School of Electrical Engineering, Aug. 1985.
Ong, S.H. et al., "Development of an Image Flow Cytometer." Analytical and Quantitative Cytology and Histology. XIVth International Conference on Medical and Biological Engineering and the VIIth International Conference on Medical Physics, Finland, Aug. 1987, 375-382.
Ong, S.H. and P.M. Nickolls, "Optical Design in a Flow System for Imaging Cells." Sciences in Medicine, Jun. 1991, 14:2:74-80.
Ortyn et al., "Extended Depth of Field Imaging for High Speed Cell Analysis" Cytometry Part A 71A: 215-231, Apr. 2007.
Pala et al., "Flow cytometric measurement of intracellular cytokines," Journal of Immunological Methods 243: 107-124,.
Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," Human Reproduction vol. 14, No. 5: 1266-1273, May 1999.
Patterson et al., "Detection ofHIV-1 DNA and Messenger RNA in Individual Cells by PCR-Driven in Situ Hybridization and Flow Cytometry," Science 260: 976-979, May 14, 1993.
Perreault et al., "The Role of Disulfide Bond Reduction during Mammalian Sperm Nuclear Decondensation in Vivo," Developmental Biology 101: 160-167, Jan. 1984.
Pinkel et al., "Cytogenetic analysis using quantitative, high sensitivity, fluorescence hybridization," Proceedings of the National Academy of Sciences: Genetics 83: 2934-2938, May 1986.
Pollice et al., "Sequential Paraformaldehyde and Methanol Fixation for Simultaneous Flow Cytometric Analysis of DNA, Cell Surface Proteins, and Intracellular Proteins," Cytometry 13: 432-444, 1992.
Ried et al., "Simultaneous visualization of seven different DNA probes by in situ hybridization using combinatorial fluorescence and digital imaging microscopy," Proceedings of the National Academy of Sciences: Genetics 89:1388-1392, Feb. 1992.
Robbins et al., "Aneuploidy in sperm of Hodgkin's disease patients receiving NOVP chemotherapy," The American Journal of Human Genetics vol. 55, No. 3- Supplement: A68 (371), Sep. 1994.
Robbins et al., "Detection of Aneuploid Human Sperm by Fluorescence In Situ Hybridization: Evidence for a Donor Difference in Frequency of Sperm Disomic for Chromosomes 1 andY," The American Journal of Human Genetics, 52: 799-807, Apr. 1993.
Robbins et al., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," Reproduction, Fertility and Development 7: 799-809, 1995.
Robbins et al., "Use of Fluorescence In Situ Hybridization (FISH) To Assess Effects of Smoking, Caffeine, and Alcohol on Aneuploidy Load in Sperm of Healthy Men," Environmental and Molecular Mutagenesis 30: 175-183, 1997.
Rufer et al., "Telomere length dynamics in human lymphocyte subpopulations measured by flow cytometry," Nature Biotechnology 16:743-747, Aug. 1998.
Salzman "Light Scatter: Detection and Usage," Current Protocols in Cytometry Supplement 9: 1.13.1-1.138.8, 1999.
Translated the Japanese Office Action mailed Sep. 9, 2011 for Japanese Patent Application No. 2007-554187, a counterpart foreign application of US patent No. 7,522,758, 2 pages.
Non-Final Office Action for U.S. Appl. No. 13/396,333, mailed on Sep. 12, 2012, William Ortyn et al., "Detection of Circulating Tumor Cells Using Imaging Flow Cytometry", 6 pages.

* cited by examiner

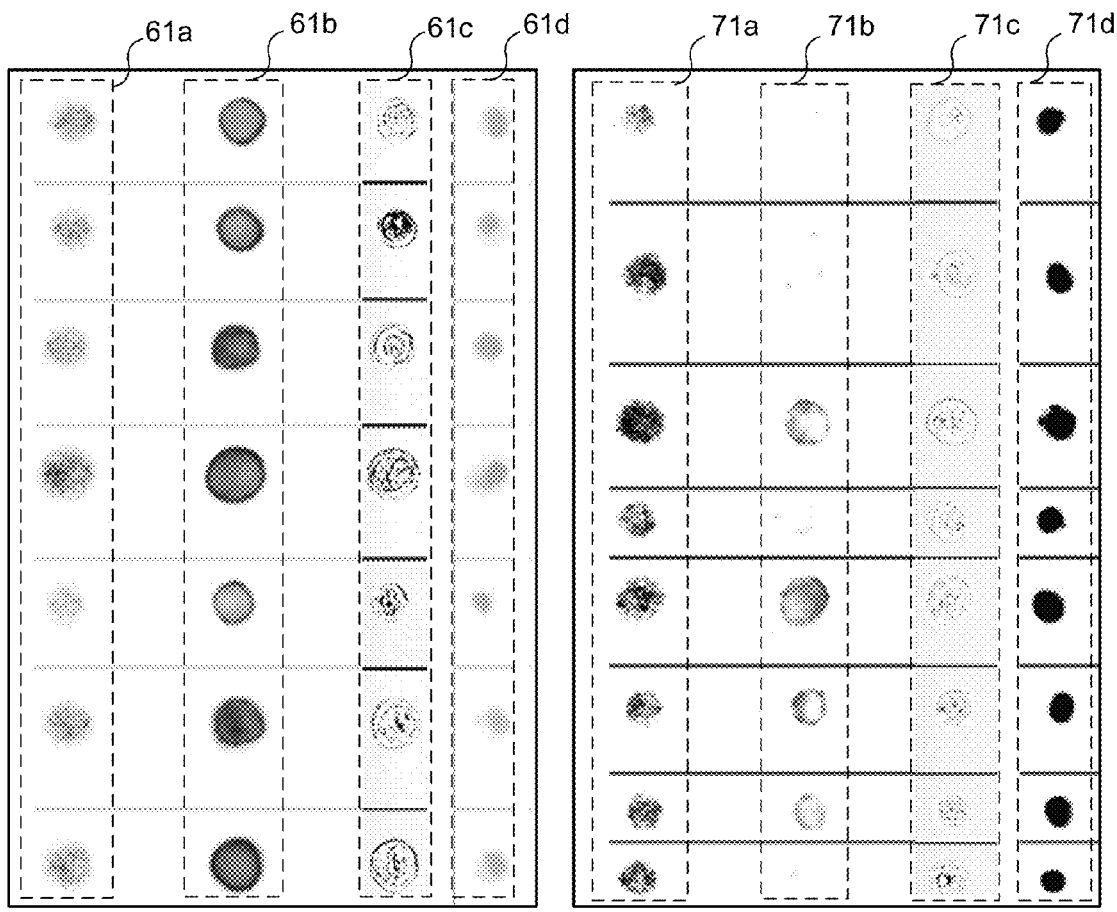
*FIG. 6*     *FIG. 7*
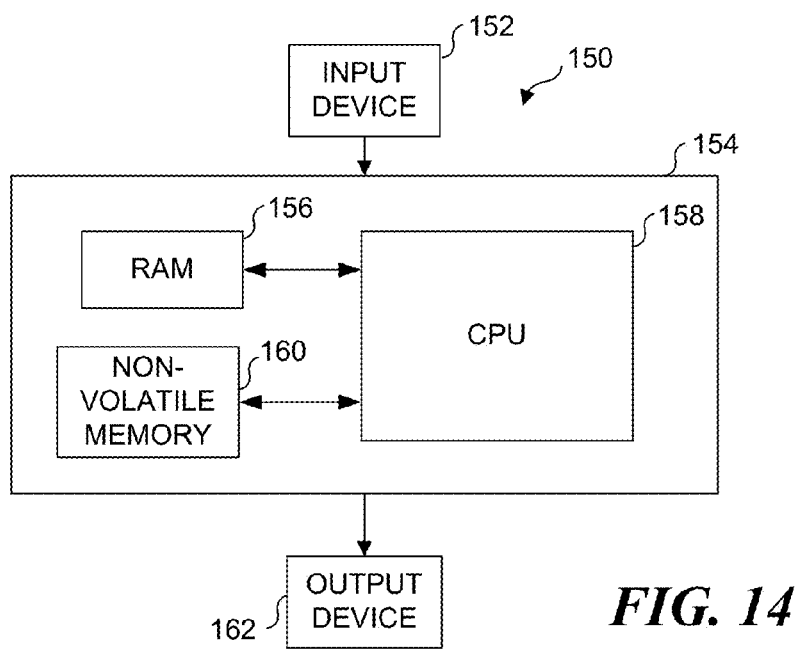
*FIG. 14*

FIG. 8A

| # | Scatter | blank | HLA-FITC | blank | Bright field | DNA | Population Statistics | Object Data | Compensation Matrix |
|---|---------|-------|----------|-------|--------------|-----|----------------------|-------------|---------------------|
| | | | | | | | Population: FITC Positive | | |
| | | | | | | | Count: 2031 | | |
| | | | | | | | Select | | |
| | | | | | | | Feature \| Median \| Mean \| Std. Dev. | | |
| | | | | | | | CV \| Min. \| Max. \| Mode \| Geo. Mean | | |
| 1105 | ● | | ● | | ▓ | ● | | | |
| 1163 | ● | | ● | | ▓ | ● | | | |

Population: Tagged FITC Positive | View: All channels with color

| SEE FIG. 8B | SEE FIG. 8C | SEE FIG. 8D | SEE FIG. 8E |
|---|---|---|---|
| SEE FIG. 8F | SEE FIG. 8G | SEE FIG. 8H | SEE FIG. 8I |
| SEE FIG. 8J | SEE FIG. 8K | SEE FIG. 8L | SEE FIG. 8M |

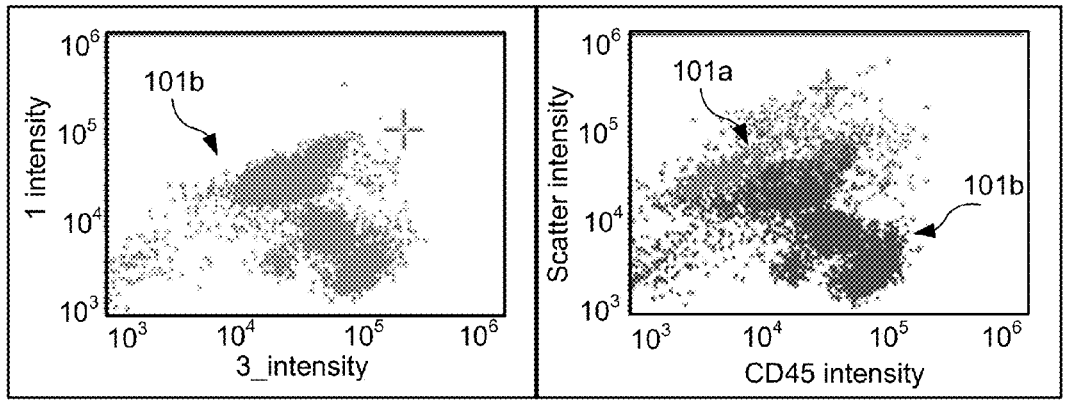
FIG. 10A  FIG. 10B
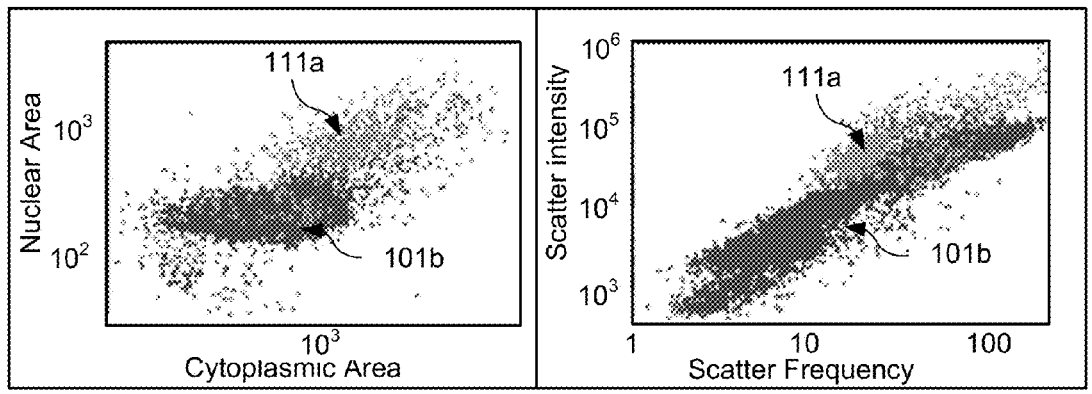
FIG. 11A  FIG. 11B
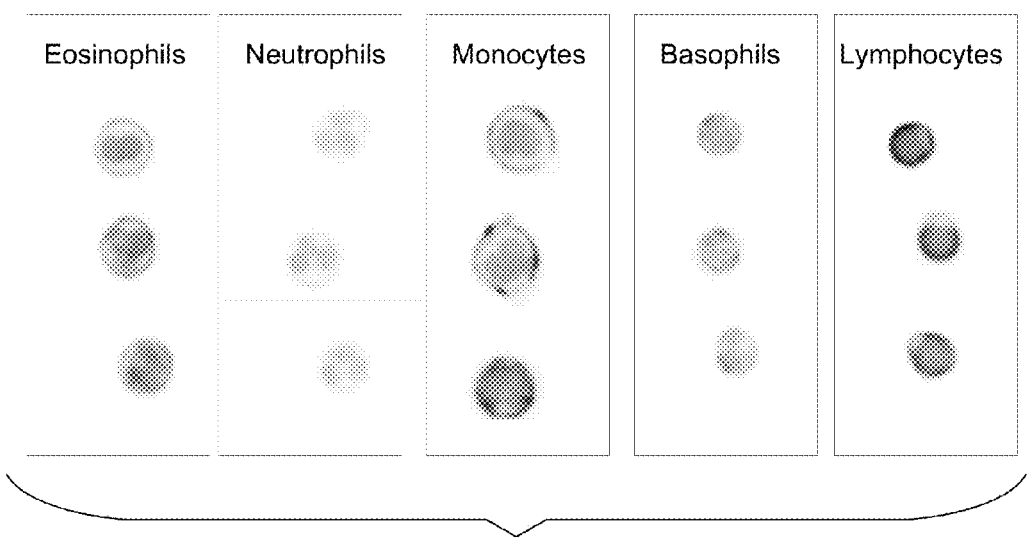
FIG. 13

BLOOD AND CELL ANALYSIS USING AN IMAGING FLOW CYTOMETER

RELATED APPLICATIONS

This application is a divisional of a continuation in part application Ser. No. 12/631,795, filed on Dec. 4, 2009 that is based on patent application Ser. No. 12/362,170, filed on Jan. 29, 2009, now U.S. Pat. No. 7,634,126, which itself is a divisional application based on patent application Ser. No. 11/344,941, filed on Feb. 1, 2006, now U.S. Pat. No. 7,522,758, the benefit of the filing date of which is hereby claimed under 35 U.S.C. §120. patent application Ser. No. 11/344,941 is based on a prior provisional application Ser. No. 60/649,373, filed on Feb. 1, 2005, the benefit of the filing date of which is hereby claimed under 35 U.S.C. §119(e). patent application Ser. No. 11/344,941 is also a continuation-in-part application based on a prior conventional application Ser. No. 11/123,610, filed on May 4, 2005, which issued as U.S. Pat. No. 7,450,229 on Nov. 11, 2008, which itself is based on a prior provisional application Ser. No. 60/567,911, filed on May 4, 2004, and which is also a continuation-in-part of prior patent application Ser. No. 10/628,662, filed on Jul. 28, 2003, which issued as U.S. Pat. No. 6,975,400 on Dec. 13, 2005, which itself is a continuation-in-part application of prior patent application Ser. No. 09/976,257, filed on Oct. 12, 2001, which issued as U.S. Pat. No. 6,608,682 on Aug. 19, 2003, which itself is a continuation-in-part application of prior patent application Ser. No. 09/820,434, filed on Mar. 29, 2001, which issued as U.S. Pat. No. 6,473,176 on Oct. 29, 2002, which itself is a continuation-in-part application of prior patent application Ser. No. 09/538,604, filed on Mar. 29, 2000, which issued as U.S. Pat. No. 6,211,955 on Apr. 3, 2001, which itself is a continuation-in-part application of prior patent application Ser. No. 09/490,478, filed on Jan. 24, 2000, which issued as U.S. Pat. No. 6,249,341 on Jun. 19, 2001, which itself is based on prior provisional patent application Ser. No. 60/117,203, filed on Jan. 25, 1999, the benefit of the filing dates of which is hereby claimed under 35 U.S.C. §120 and 35 U.S.C. §119(e). patent application Ser. No. 09/976,257, noted above, is also based on prior provisional application Ser. No. 60/240,125, filed on Oct. 12, 2000, the benefit of the filing date of which is hereby claimed under 35 U.S.C. §119(e).

GOVERNMENT RIGHTS

This invention was funded at least in part with a grant (No. R43 CA 94590-01) from the National Cancer Institute, and the U.S. government may have certain rights in this invention.

BACKGROUND

Cellular hematopathologies have been traditionally identified and studied by a variety of slide based techniques that include morphological analysis of May-Grunwald/Giemsa or Wright/Giemsa stained blood films and cytoenzymology. Additionally, other techniques, such as cell population analysis by flow cytometry, and molecular methods, such as polymerase chain reaction (PCR) or in situ hybridization to determine gene expression, gene mutations, chromosomal translocations and duplications, have added to the understanding of these pathologies.

Although progress has been made using such techniques in advancing diagnostic capabilities, understanding the mechanisms and the progression of disease, as well as evaluating new therapeutics, such technologies each offer challenges with regard to standardization and robustness, and to a large degree, they have not yet evolved to become routine laboratory tests.

The conventional hematology clinical laboratory includes technologies to rapidly and automatically analyze large numbers of samples of peripheral blood, with minimal human intervention. Companies such as Abbott Laboratories (Abbott Park, Ill.), Beckman Coulter Inc. (Fullerton, Calif.), and TOA Corporation (Kobe, Japan) continue to advance these technologies with regard to throughput levels, the degree of accuracy of the analysis, as well as moderately increasing the information content gathered in each sample run. However, in regard to any sample suggestive of a cellular hematopathology, i.e., falling outside the accepted degree of variance for any particular parameter, traditional slide based methodologies are largely used to determine the probable cause of the abnormality.

Diagnostic criteria in hematology are based on the morphological identification of abnormalities in cell numbers, size, shape and staining patterns. Although these have been supplemented over the past decades with cell population analysis, by staining with monoclonal antibodies to various cell surface determinants and acquiring data via flow cytometry, the most important element in the diagnostic evaluation is the visual inspection of the peripheral blood film, bone marrow and lymph node biopsy using a microscope, which enables a subjective categorization of putative abnormalities.

The manual evaluation of tissue and blood films from patients is tedious, time consuming, and subject to significant intra-laboratory and intra-observer variability. This process suffers from many sources of variability and error, including staining variability (which adversely affects longitudinal analysis), bias of the evaluator, and suboptimal sample preparation (blood films with increased "smudge" cells and atypical lymphocytes). The manual classification of a few hundred cells by morphological appearance results in poor statistical power and low confidence in evaluating observed changes over time, or as a result of treatment.

Chronic lymphocytic leukemia (CLL) is a type of cancer in which the bone marrow produces an excess of lymphocytes (a type of white blood cell) due to a malignant transformation event (e.g., chromosomal translocation). CLL is the most frequent type of leukemia in the Western world. Normally, stem cells (immature cells) develop into mature blood cells by a process of ordered differentiation, which occurs in the bone marrow. There are three types of mature blood cells: (1) red blood cells that carry oxygen to all tissues of the body; (2) white blood cells that fight infection; and, (3) platelets that help prevent bleeding by forming blood clots. Normally, the numbers and types of these blood cells are tightly regulated. In CLL, there is a chronic pathological overproduction of a type of white blood cell called lymphocytes. There are three types of lymphocytes: (1) B lymphocytes that make antibodies to help fight infection; (2) T lymphocytes that help B lymphocytes make antibodies to fight infection; and, (3) killer cells that attack cancer cells and viruses. CLL is a disease involving an increase in B lymphocyte cell numbers in the peripheral blood, usually reflective of a clonal expansion of a malignantly transformed CD5+ B lymphocyte cell.

Currently, established chemotherapeutic treatments are used to treat this condition, but a number of newer therapeutics, involving monoclonal antibodies to cell surface antigens expressed on CLL cells (e.g., Rituximab), have been developed. Recent data from the National Cancer Data Base indicate that the 5-year survival for this disease condition is about 48%, with only 23% of patients surviving the disease condition after 10 years. Recently, a number of prognostic factors have been identified that allow stratification of the patient population into two subpopulations with distinct clinical outcomes. Factors that tend to correlate with decreased survival are: ZAP70 expression (a tyrosine kinase required for T lymphocyte cell signaling), increased CD38 expression, un-mutated IgVh genes, and chromosomal abnormalities. However, routine assessment of these factors has not evolved to a standard clinical practice, due to technical challenges with data standardization and interpretation.

Morphological evaluation remains the "gold standard" in the assessment of hematopathologies, and patients with CLL present with morphological heterogeneity. Attempts to correlate a particular morphological profile with clinical prognosis have been made, but to date, no association has been widely accepted, and the morphologic sub-classification of CLL and its correlation with clinical prognosis remains to be explored.

It would therefore be desirable to provide a method and apparatus suitable for automatically analyzing blood, including peripheral blood leukocytes, and cellular components such as bone marrow and lymph nodes (whose cells are readily amenable to being processed in suspension), to facilitate researching blood related diseases and abnormalities. It would be particularly desirable to provide a method and apparatus for rapidly collecting imagery from blood and other bodily fluids (and cellular compartments), and to provide software tools for analyzing such imagery to identify cellular abnormalities or cellular distribution abnormalities associated with a disease condition.

SUMMARY

This application specifically incorporates by reference the disclosures and drawings of each patent application and each issued patent identified above as a related application.

Aspects of the concepts disclosed herein relate to the collection of multispectral images from a population of cells, and the analysis of the collected images to measure at least one characteristic of the population, using photometric and/or morphometric image features calculated from the collection of images, where the image feature is associated with a disease condition. In an exemplary application, the cells are obtained from bodily fluids and cellular compartments, and in a particularly preferred implementation, from blood, most preferably where the cellular compartments are bone marrow and lymph nodes. In a further particularly preferred implementation, both photometric and morphometric image features are used in the analysis. In a particularly preferred, but not limiting implementation, the plurality of images for each individual object are collected simultaneously.

Exemplary steps that can be used to analyze biological cells in accord with an aspect of the concepts disclosed herein includes collecting image data from a population of cells, and identifying one or more subpopulations of cells from the image data. In one implementation, a subpopulation corresponding to cells exhibiting abnormalities associated with a disease condition is identified. Such subpopulations can be identified based on empirical evidence indicating that one or more photometric and/or morphometric image features are typically associated with the cellular abnormality associated with the disease condition. The term "image feature" is intended to refer to a calculated value that quantitatively characterizes a particular structure, region, visual property, biochemical abundance, biochemical location, or other aspect of a cell that can be readily discerned from one or more images of the cell. The photometric and/or morphometric image features calculated from the collected images are analyzed to enable at least one characteristic of a cell or population of cells to be measured. Cellular characteristics that have been empirically associated with the cellular abnormalities present during a particular disease condition (e.g. an increase in expression of a particular cell surface protein (which can be labeled with a marker) as measured using a photometric "intensity" image feature or an increase in cell size as measured using a morphometric "cell area" image feature) can be detected in the data to determine whether a particular disease condition is present in the population of cells originally imaged.

In yet another exemplary implementation, a disease condition may be detected even when the cells themselves do not exhibit any abnormalities that can be identified by photometric and/or morphometric image features. In such an implementation, a sample will include a plurality of different subpopulations, each of which is identified by its normal characteristic morphometric and photometric image features. Where a disease condition is not present, the ratio of the subpopulations relative to one another will vary within a determinable range across different patients. Where a disease condition is present, the disease condition can alter the ratio of subpopulations, such that a change in the ratio beyond a normal range can indicate the presence of a disease condition. Consider a population of blood cells from a healthy patient. The ratio of lymphocytes to other types of blood cells can be determined by analyzing image data of the entire population of blood cells to classify the images according to blood cell type. When this same process is applied to a population of blood cells from a patient with CLL, the ratio of lymphocytes to other types of blood cells will be significantly different than the ratio identified in a patient not afflicted with CLL. Thus, a disease condition can be detected by analyzing a population of cells to identify subpopulations present in the population, and by determining changes in the ratios of the subpopulations that suggest the presence of a disease condition.

In yet another exemplary implementation, a disease condition may be detected by the presence of an uncharacteristic cell type. In such an implementation, a sample will include a plurality of different subpopulations, each of which is identified by its characteristic morphometric and photometric image features. Where a disease condition is not present, only the expected subpopulations will be evident within the sample, though they may vary within a normal range across different patients. Where a disease condition is present, an entirely atypical cell type may be evident in the sample. For example, metastatic cancer of the breast may be evidenced by the presence of distinctive epithelial cells at some level in the blood. Thus, a disease condition can be detected by analyzing a population of cells to identify subpopulations present in the population, and determining the prevalence of atypical subpopulations that suggest the presence of a disease condition. The disease condition may be further refined by analyzing the morphometric and photometric image features of the atypical cell population to determine its tissue of origin or metastatic state. For example, the presence of a large fraction of rapidly dividing cells, as evidenced by a high nuclear to cellular size ratio image feature, may characterize a circulating tumor cell as aggressive.

In still another exemplary implementation, a disease condition may be detected by the analysis not only of the cell subpopulations and their relative abundance, but also by an analysis of free (not cell-associated) bio-molecules within the cell sample. In such an implementation, a reagent may be added to the cell sample, the reagent comprising reactive substrates, each of which indicates the amount of a particular bio-molecule present in the sample. Each reactive substrate (e.g., a microsphere) includes a unique optical signature that identifies the species of bio-molecule to which it preferentially binds, as well as potentially indicating the amount of that bio-molecule in the sample. By analyzing the imagery of a co-mingled sample of reactive substrates and cells, the former may be distinguished from the latter, and both a molecular and cellular analysis can be performed on the sample in a multiplexed fashion.

Image data for the population and subpopulation(s) can be manipulated using several different techniques. An exemplary technique is referred to as gating, which is a method of graphically defining a sub-population of cells on a histogram or scatter plot of photometric or morphometric cell image features for a given cell population. A further exemplary technique is backgating, in which a previously-defined sub-population is graphically highlighted on a histogram or scatter plot of photometric or morphometric cell image features of a cell population. While not strictly required, signal processing is preferably performed on the collected image data to reduce crosstalk and enhance spatial resolution, particularly for image data collected using simultaneous multi-channel imaging.

In an exemplary implementation, image data is collected from two different populations of cells (noting that image data of either of the two different populations can also be compared to image data of other cell populations if desired). The image data is analyzed to identify image features that quantify differences between the two different cell populations. Many different strategies can be employed in selecting the two different cell populations. In some embodiments, the first cell population will include some known anomaly, and the second population will be known to be normal (or at least known to correspond to a baseline cell population, where the anomalous cell population is somehow manipulated or exposed to some factor, and the baseline cell population has not been similarly manipulated or exposed), enabling differences between the two populations to be quantified using the image data. The anomaly can include, but is not limited to, the presence of neoplastic cells, the presence of necrotic cells, the presence of cells exposed to a toxic agent, the presence of cells exposed to a therapeutic agent, the presence of cells exposed to a stimulating agent, the presence of cells exposed to a chemical agent, the presence of cells exposed to a viral agent, the presence of cells exposed to a bacterial agent, the presence of cells exposed to a nutrient, the presence of cells exposed to an environmental change, and the presence of different cells whose relative abundance is associated with an anomalous condition.

The two different populations of cells can be acquired from different sources. For example, the anomalous cell population can be acquired from a person suffering some condition, and the baseline or normal cell population can be acquired from a healthy person. In an other example, the anomalous cell population can be acquired from a prepubescent male or female, and the baseline or normal cell population can be acquired from a post pubescent male or female (noting that in this case, it does not matter whether the prepubescent cells or adult cells are considered to represent the anomalous or baseline population).

The two different populations of cells can be acquired from the same source, at the same time, with the anomalous cell population being manipulated or exposed to some agent, and the baseline or normal cell population not being similarly manipulated or exposed.

The two different populations of cells can be acquired from the same source, at different times, to aid in quantifying cellular changes over time. In this case, it does not matter whether the relatively older sample or the relatively newer sample is considered to represent the anomalous or baseline population. In addition to simply a passage of time, some other factor may contribute to some change in the cell populations. The factor can include a change in diet, a change in stress, a change in environmental conditions, a change in health, exposure to environmental factors, exposure to therapeutic agents, exposure to toxins, exposure to viruses, exposure to infectious agents, and many other factors.

Yet another aspect of the techniques disclosed herein relates to monitoring the treatment of a patient exhibiting a disease condition. Baseline data are collected by imaging a population of cells from the patient before treatment. For example, the population of cells can be obtained from a bodily fluid, such as blood. During the course of treatment, additional data are obtained by imaging additional populations of cells collected from the patient during and after various stages of the treatment process. Such data will provide a quantitative indication of the improved condition of the patient suffering from the disease condition, as indicated by either the amount of cells expressing the disease condition versus normal cells, or by a change in a ratio of the subpopulations present in the population. Significantly, such quantification is not feasible with standard microscopy and/or conventional flow cytometry.

In another exemplary implementation of the techniques disclosed herein, the imagery collected from a population of biological cells includes collection of multimodal images. That is, the images collected will include at least two of the following types of images: one or more images corresponding to light emitted from the cell (e.g. a fluorescence image), one or more images corresponding to light transmitted by the cell (e.g. a bright field image), and one or more images corresponding to light scattered by the cell (e.g. a dark field image). Such multimode imaging can encompass any of the following types of images or combinations thereof: (1) one or more fluorescence images and at least one bright field image; (2) one or more fluorescence images and at least one dark field image; (3) one or more fluorescence images, a bright field image, and a dark field image; and (4) a bright field image and a dark field image. Simultaneous collection of a plurality of different fluorescence images (separated by spectrum) can also be beneficial, as well as simultaneous collection of a plurality of different bright field images (for example, using transmitted light with two different spectral filters). The multimode images can preferably be collected simultaneously.

As discussed above, image data for a plurality of images of individual cells that are acquired simultaneously can be used to detect a disease condition. Note that such an application is based on identifying and/or quantifying differences between a first cell population and a second cell population, by analyzing the image data collected for each cell population. Generally, as described above, the image data can be analyzed to identify quantifiable photometric and morphometric differences between the first and second cell populations. The image data can also be used to identify a cell type present in one of the first and second cell populations, but not the other of the first and second cell populations. Similarly, the image data can also be used to identify differences in the relative distribution of cell types in the first and second cell populations, to determine if there is more or less of a particular cell type in the first population of cells, as compared to the second population of cells (and vice versa). These techniques can provide diagnostic information about a patient from whom the cells are obtained, beyond simply determining if a specific disease condition exists.

In one exemplary embodiment, the first and second population of cells are obtained from a person at different times. In another exemplary embodiment, the first and second population of cells are obtained from a person at the same time, but then treated differently before being imaged as described above. For example, a single blood sample or bodily fluid sample can be acquired from a person, and that sample can be split into two fractions for different treatment prior to imaging. Image data for the first fraction (the first population of cells) can be acquired. The second fraction (i.e., the second population of cells) can be exposed to a stimulus before image data are acquired. The image data from the first and second populations of cells can then be analyzed to determine how the cell populations have changed.

In one related embodiment, image data from a first population of cells and a second population of cells are analyzed to determine if variations in a specific cell type present in both populations exist, regardless of whether those differences are indicative of a disease condition. This technique is generally directed at acquiring the first and second cell populations from a person at different times, and determining if there are differences between the same cell type in the first and second populations due to changes over time. If data are available indicating the conditions experienced by the person during the time between acquiring the samples (e.g. a change in medication), then an attempt to correlate the changes to such conditions can be performed. Even where no such correlations can be found, any changes identified may be indicative of changes in the health of the person. For example, some cellular changes may suggest that the health of the patient has improved or declined, even if no specific disease condition is identified. Furthermore, even if no change in the first and second cell populations is identified, that determination may itself represent valuable diagnostic data, either indicating that the health of the person has not appreciably changed, or if the person's health has changed, indicating that the specific cell type is likely not related to the change in health.

In another exemplary embodiment, image data from a first population of cells and a second population of cells are analyzed to determine if there has been a change in the relative distribution of different types of cells present in both populations, where such a change is not limited to being indicative of a specific disease condition, but may still be relevant to the health of the person from whom the first and second cell populations were obtained. This analysis includes determining if a specific cell type is present in the first cell population, but not the second cell population, and vice versa, as well as determining how the relative percentages of cell types present in both the first and second cell populations has changed. This technique is generally directed at acquiring the first and second cell populations from a person at different times, and determining if there are differences between the distribution of different cell types in the first and second populations. If data are available indicating the conditions experienced by the person during the time between acquiring the samples, then an attempt to correlate the changes to such conditions can be performed. Even where no such correlations can be found, any changes identified may be indicative of the health of the person. For example, some cell signaling molecule distribution changes may suggest that the health of the patient has improved or declined, even if no specific disease condition is identified. Furthermore, even if no change in the cell signaling molecule distributions in the first and second cell populations is identified, that itself may be valuable diagnostic data, either indicating that the health of the person has not appreciably changed, or if the person's health has changed, indicating that the molecule distribution analyzed is likely not related to the change in health.

In another exemplary embodiment, image data from a first population of cells and a second population of cells are analyzed to determine how the second population of cells responds to a stimulus not applied to the first population of cells, in order to either detect a disease condition or to collect information relevant to the health of the person from whom the populations of cells were obtained, without specifically identifying a disease condition. In general, this technique is based on acquiring one sample from a person, and splitting that sample into two different fractions (the two different cell populations can be acquired from the person at different times, however doing so will introduce an additional variable). The first population of cells acts as a control. A stimulus is applied to the second population of cells so that the effect of the stimulus on the cells can be determined by comparing data collected for the two populations.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 3:
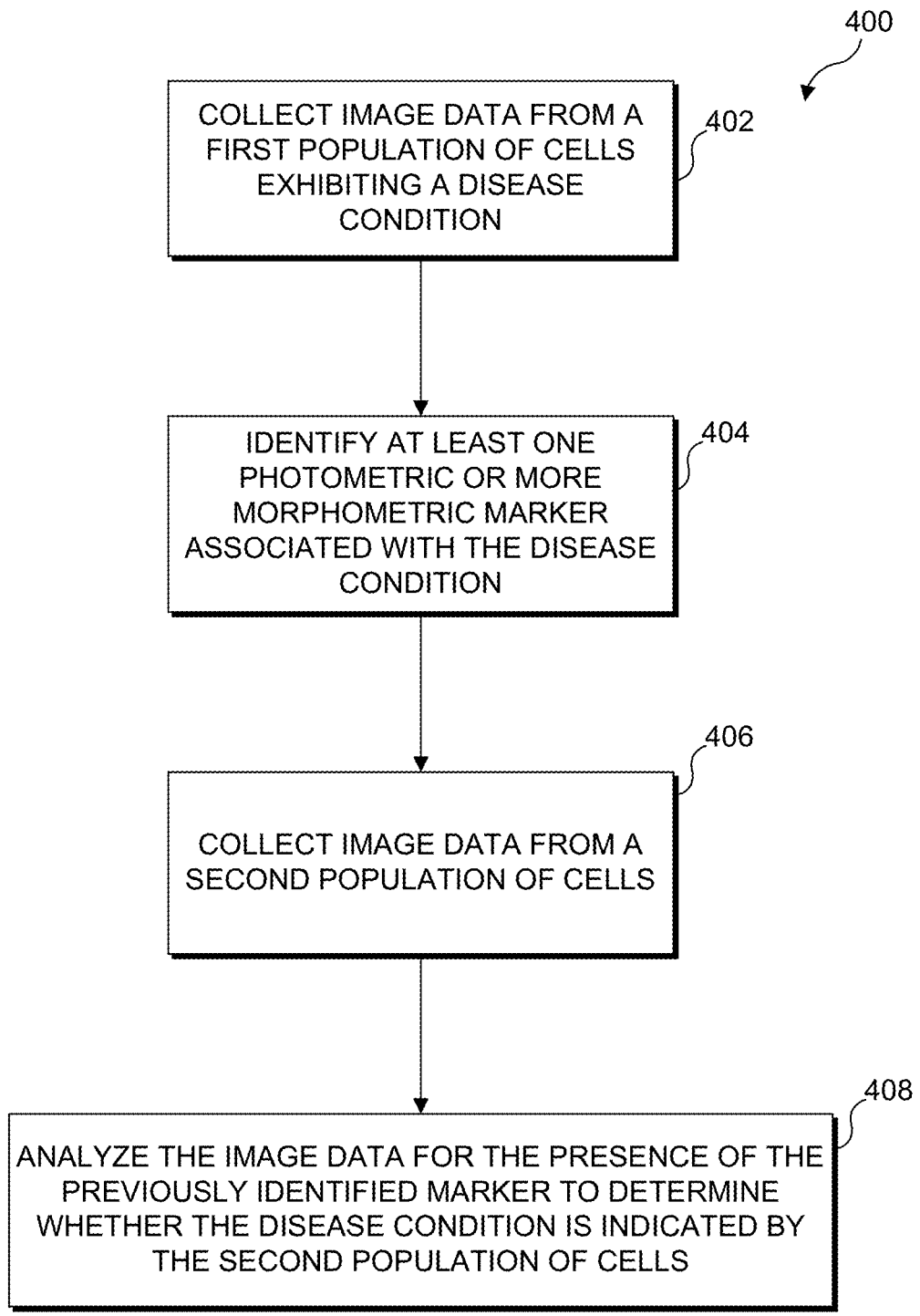
FIG. 3 is a flow chart of the overall method steps implemented in one aspect of the concepts disclosed herein.
Figure 8B:
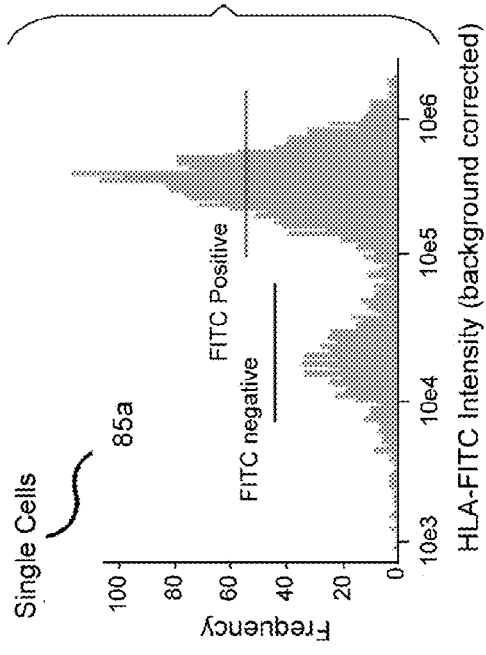
Figure 9:
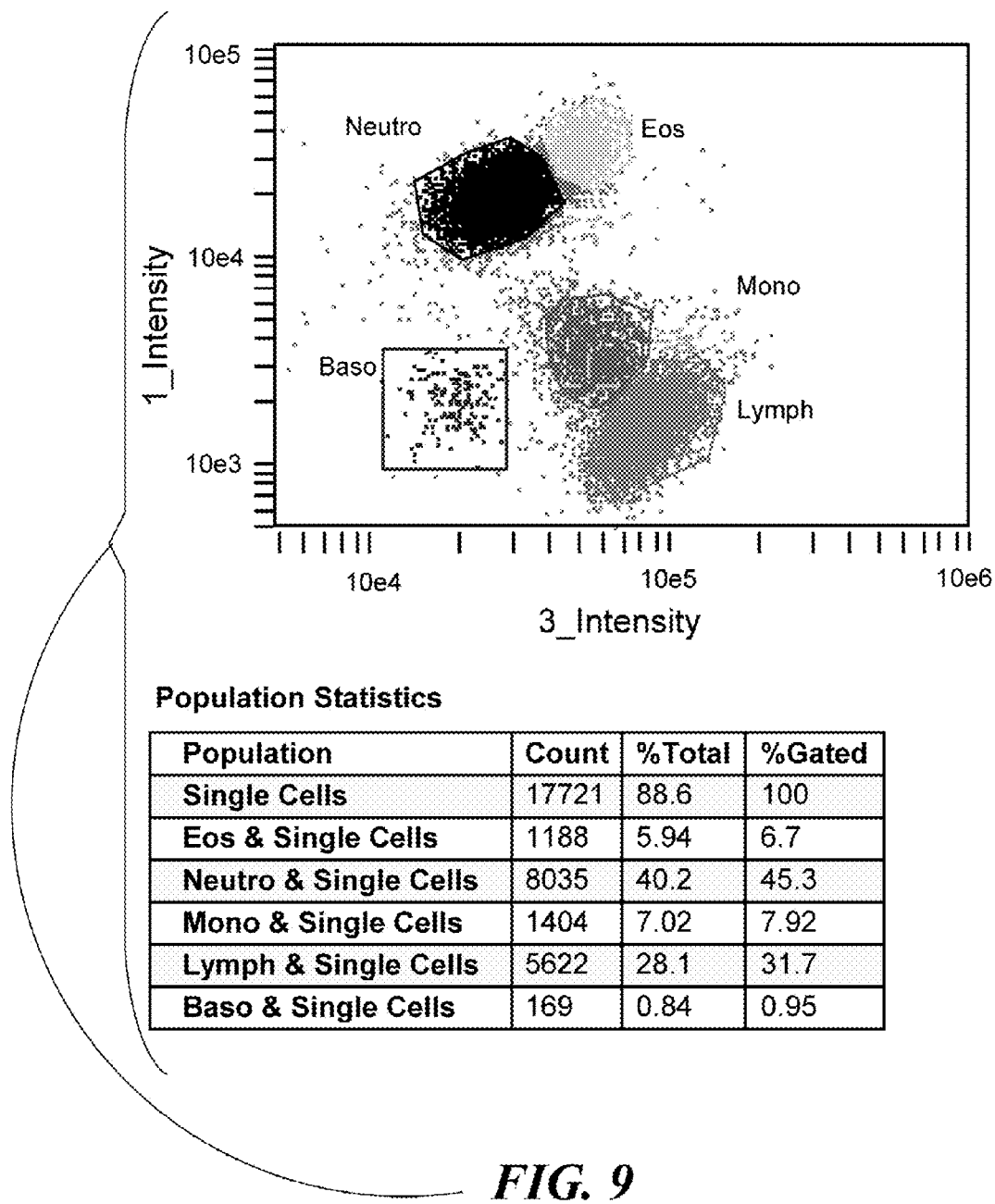
Figure 12:
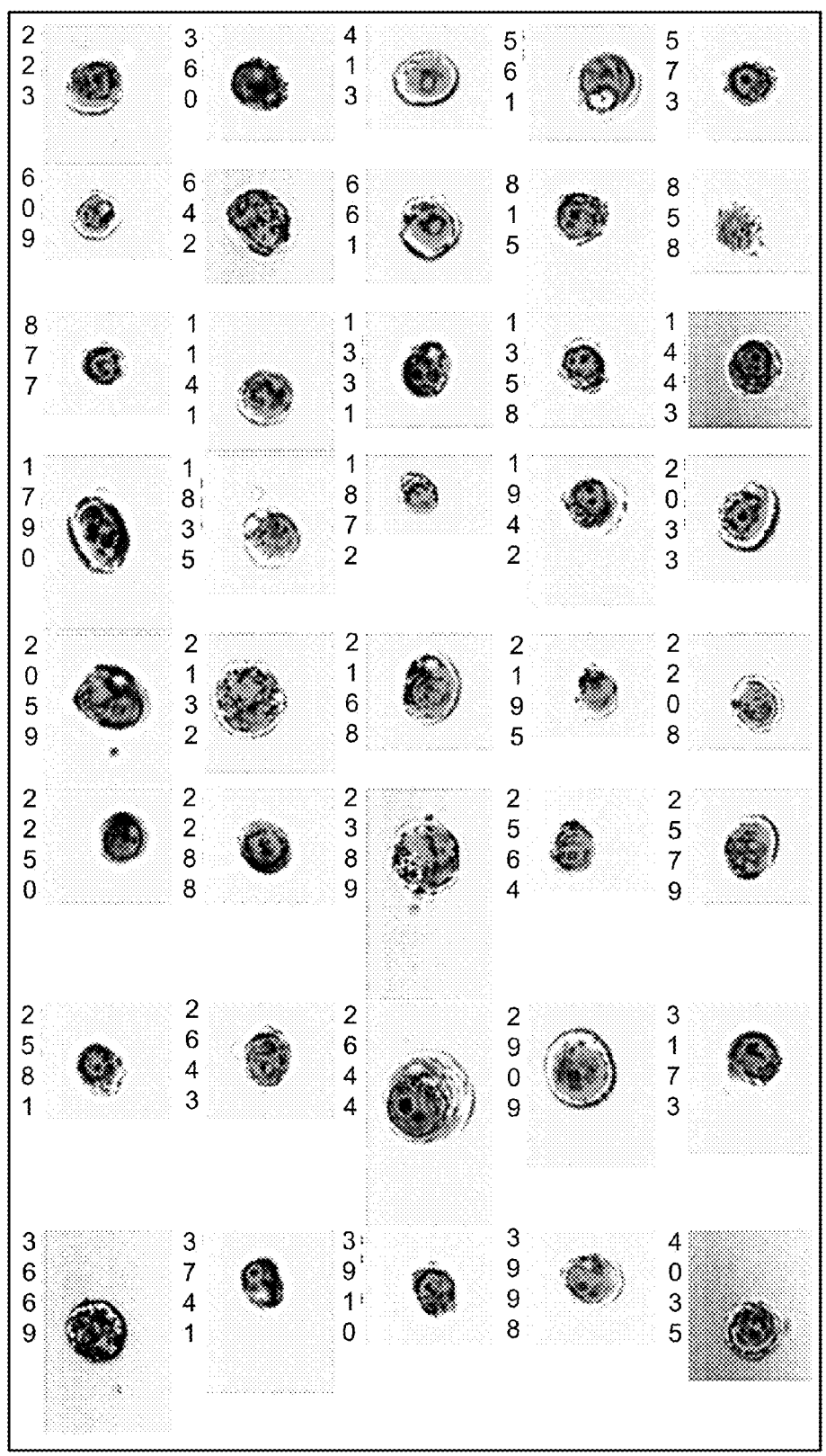
Figure 15:
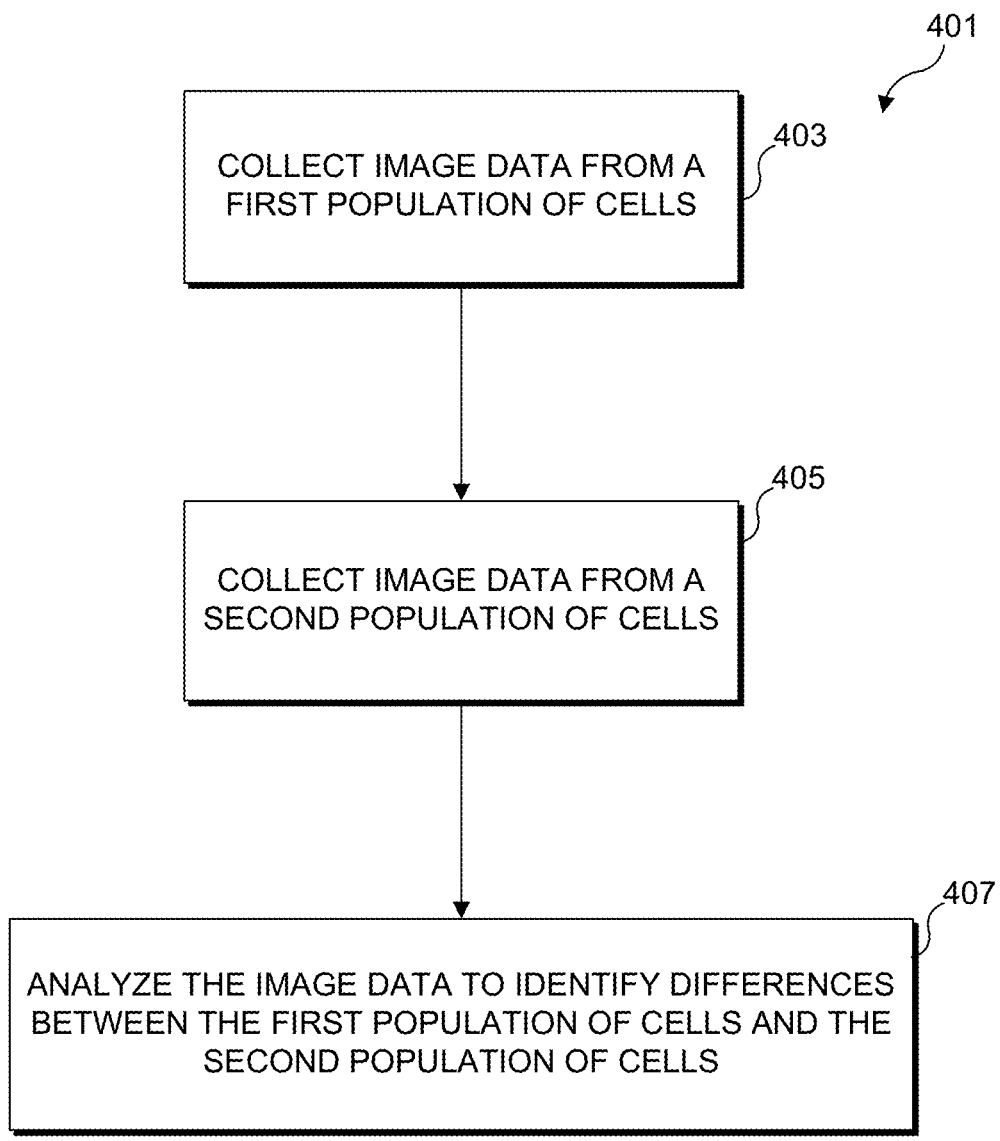

FIG. 6 includes images of normal (i.e., healthy) mammary epithelial cells;

FIG. 7 includes images of mammary carcinoma (i.e., diseased) cells, illustrating how quantification of data in a fluorescent channel serves as an image feature for the disease condition;

FIG. 8A is an exemplary graphical user interface used to implement the method steps of FIG. 3, illustrating a plurality of different photometric and morphometric descriptors as shown in FIGS. 8B-8M that can be used to automatically distinguish images of healthy mammary epithelial cells from images of mammary carcinoma cells;

FIG. 9 graphically illustrates the separation of cells in human peripheral blood into a variety of subpopulations based on photometric properties;

FIG. 10A graphically illustrates a distribution of normal peripheral blood mononuclear cells (PBMC) based on image data collected from a population of cells that do not include mammary carcinoma cells;

FIG. 10B graphically illustrates a distribution of normal PBMC and mammary carcinoma cells based on image data collected from a population of cells that includes both cell types, illustrating how the distribution of mammary carcinoma cells is distinguishable from the distribution of the normal PBMC cells;

FIG. 11A graphically illustrates a distribution of normal PBMC and mammary carcinoma cells based on a measured cytoplasmic area derived from image data collected from a population of cells that includes both cell types, illustrating how the distribution of cytoplasmic area of the mammary carcinoma cells is distinguishable from the distribution of cytoplasmic area of the normal PBMC cells;

FIG. 11B graphically illustrates a distribution of normal PBMC and mammary carcinoma cells based on measured scatter frequency derived from image data collected from a population of cells that includes both cell types, illustrating how the distribution of the scatter frequency of the mammary carcinoma cells is distinguishable from the distribution of the scatter frequency of the normal PBMC cells;

FIG. 12 shows composite images of cells generated by combining bright field and fluorescent images of mammary carcinoma cells;

FIG. 13 shows representative images of five different PBMC populations that can be defined by scatter data derived from image data of a population of cells;

FIG. 14 schematically illustrates an exemplary computing system used to implement the method steps of FIG. 3; and FIG. 15 is a flow chart illustrating exemplary steps for analyzing two populations of cells, based on images of the cell populations, in order to identify and/or quantify differences between the cell populations.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive.

Overview

The present disclosure encompasses a method of using flow imaging systems that can combine the speed, sample handling, and cell sorting capabilities of flow cytometry with the imagery, sensitivity, and resolution of multiple forms of microscopy and full visible/near infrared spectral analysis to collect and analyze data relating to disease conditions in blood, particularly detecting and monitoring chronic lymphocytic leukemia.

An aspect of the concepts disclosed herein relates to a system and method for imaging and analyzing biological cells entrained in a flow of fluid. In at least one embodiment, a plurality of images of biological cells are collected simultaneously; the plurality of images including at least two of the following types of images: a bright field image, a dark field image, and a fluorescent image. Images are collected for a population of biological cells. Once the imagery has been collected, the images can be processed to identify a subpopulation of images, where the subpopulation shares photometric and/or morphometric characteristics empirically determined to be associated with a disease condition.

With respect to the following disclosure, and the claims that follow, it should be understood that the term "population of cells" refers to a group of cells including a plurality of objects. Thus, a population of cells must include more than one cell.

A preferred imaging system to be used in collecting the image data required to implement the techniques disclosed herein will incorporate the following principal characteristics:

1. high speed measurement;
2. the ability to process very large or continuous samples;
3. high spectral resolution and bandwidth;
4. good spatial resolution;
5. high sensitivity; and
6. low measurement variation.

In particular, a recently developed imaging flow cytometer technology, which is embodied in an ImageStream™ instrument (Amnis Corporation, Seattle, Wash.), makes great strides in achieving each of the above-noted principle characteristics. The ImageStream™ instrument is a commercial embodiment of the flow imaging systems described below in detail with respect to FIG. 1. These significant advancements in the art of flow cytometery are described in the following commonly assigned patents: U.S. Pat. No. 6,249,341, issued on Jun. 19, 2001 and entitled "Imaging And Analyzing Parameters of Small Moving Objects Such As Cells;" U.S. Pat. No. 6,211,955 issued on Apr. 3, 2001, also entitled "Imaging And Analyzing Parameters of Small Moving Objects Such As Cells;" U.S. Pat. No. 6,473,176, issued on Oct. 29, 2002, also entitled "Imaging And Analyzing Parameters of Small Moving Objects Such As Cells;" U.S. Pat. No. 6,583,865, issued on Jun. 24, 2003, entitled "Alternative Detector Configuration And Mode of Operation of A Time Delay Integration Particle Analyzer;" U.S. patent application Ser. No. 09/989,031 entitled "Imaging And Analyzing Parameters of Small Moving Objects Such As Cells in Broad Flat Flow." While the ImageStream™ platform represents a particularly preferred imaging instrument used to acquire the image data that will be processed in accord with the concepts disclosed herein, it should be understood that the concepts disclosed herein are not limited only to the use of that specific instrument.

As noted above, in addition to collecting image data from a population of biological cells, an aspect of the concepts disclosed herein involves processing the image data collected to measure at least one characteristic associated with a disease condition in the imaged population. A preferred image analysis software package is IDEAS™ (Amnis Corporation, Seattle, Wash.). The IDEAS™ package evaluates nearly 200 image features for every cell, including multiple morphologic and fluorescence intensity measurements, which can be used to define and characterize cell populations. The IDEAS™ package enables the user to define biologically relevant cell subpopulations, and analyze subpopulations using standard cytometry analyses, such as gating and backgating. It should be understood, however, that other image analysis methods or software packages can be implemented to apply the concepts disclosed herein, and the preferred image analysis software package that is disclosed is intended to be exemplary, rather than limiting of the concepts disclosed herein.

Overview of a Preferred Imaging System

Figure 1A:
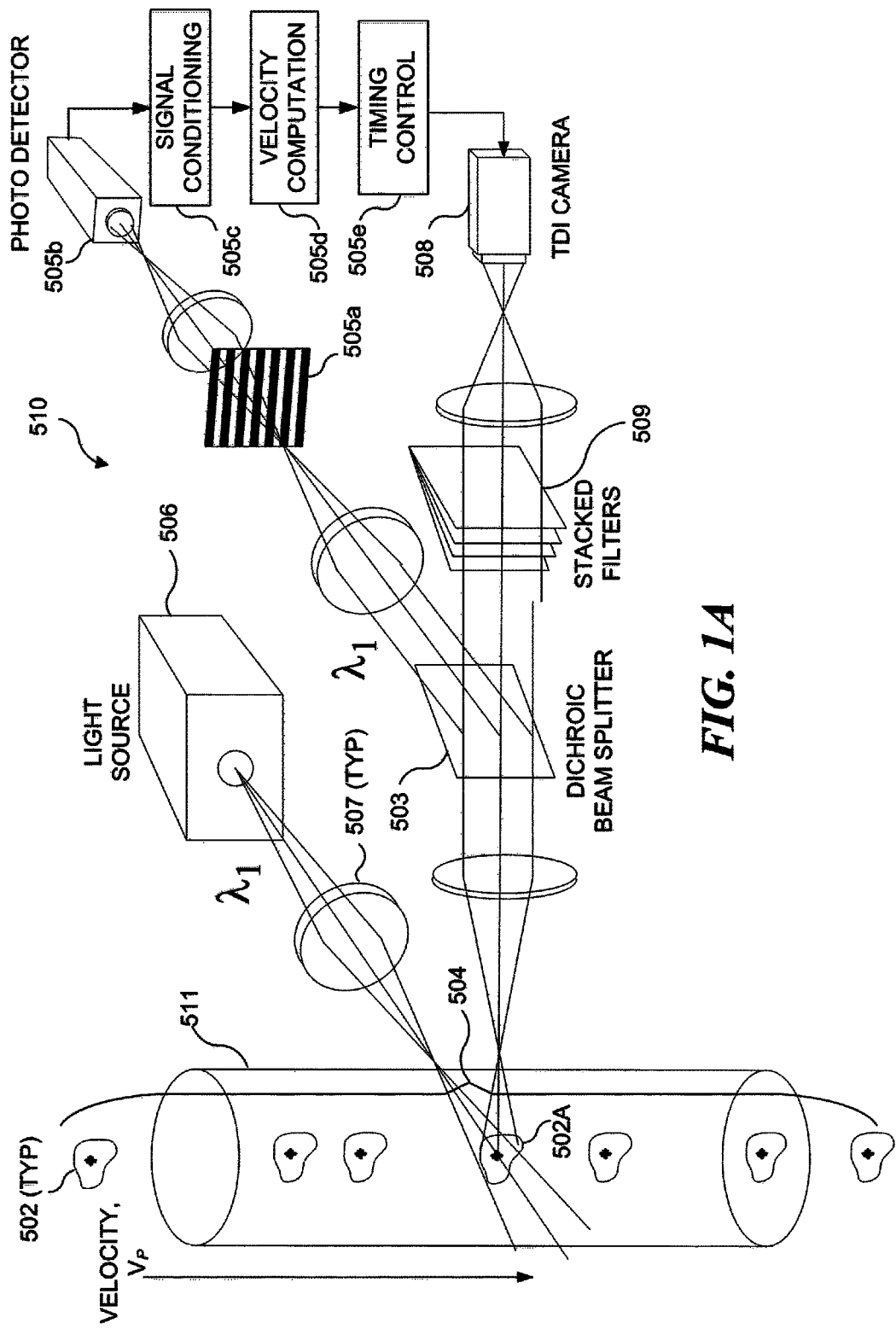
FIG. 1A is a schematic diagram of an exemplary flow imaging system that can be used to simultaneously collect a plurality of images from an object in flow.

FIG. 1 is a schematic diagram of a preferred flow imaging system 510 (functionally descriptive of the ImageStream™ platform) that uses TDI when capturing images of objects 502

(such as biological cells), entrained in a fluid flow 504. System 510 includes a velocity detecting subsystem that is used to synchronize a TDI imaging detector 508 with the flow of fluid through the system. Significantly, imaging system 510 is capable of simultaneously collecting a plurality of images of an object. A particularly preferred implementation of imaging system 510 is configured for multi-spectral imaging and can operate with six spectral channels: DAPI fluorescence (400-460 nm), Dark field (460-500 nm), FITC fluorescence (500-560 nm), PE fluorescence (560-595 nm), Bright field (595-650 nm), and Deep Red (650-700 nm). The TDI detector can provide 10 bit digital resolution per pixel. The numeric aperture of the preferred imaging system is typically 0.75, with a pixel size of approximately 0.5 microns. However, those skilled in the art will recognize that this flow imaging system is neither limited to six spectral channels, nor limited to either the stated aperture size or pixel size and resolution.

Moving objects 502 are illuminated using a light source 506. The light source may be a laser, a light emitting diode, a filament lamp, a gas discharge arc lamp, or other suitable light emitting source, and the system may include optical conditioning elements such as lenses, apertures, and filters that are employed to deliver broadband or one or more desired wavelengths or wavebands of light to the object with an intensity required for detection of the velocity and one or more other characteristics of the object. Light from the object is split into two light paths by a beam splitter 503. Light traveling along one of the light paths is directed to the velocity detector subsystem, and light traveling along the other light path is directed to TDI imaging detector 508. A plurality of lenses 507 are used to direct light along the paths in a desired direction, and to focus the light. Although not shown, a filter or a set of filters can be included to deliver to the velocity detection subsystem and/or TDI imaging detector 508, only a narrow band of wavelengths of the light corresponding to, for example, the wavelengths emitted by fluorescent or phosphorescent molecules in/on the object, or light having the wavelength(s) provided by the light source 506, so that light from undesired sources is substantially eliminated.

The velocity detector subsystem includes an optical grating 505a that amplitude modulates light from the object, a light sensitive detector 505b (such as a photomultiplier tube or a solid-state photodetector), a signal conditioning unit 505c, a velocity computation unit 505d, and a timing control unit 505e, which assures that TDI imaging detector 508 is synchronized to the flow of fluid 504 through the system. The optical grating preferably comprises a plurality of alternating transparent and opaque bars that modulate the light received from the object, producing modulated light having a frequency of modulation that corresponds to the velocity of the object from which the light was received. Preferably, the optical magnification and the ruling pitch of the optical grating are chosen such that the widths of the bars are approximately the size of the objects being illuminated. Thus, the light collected from cells or other objects is alternately blocked and transmitted through the ruling of the optical grating as the object traverses the interrogation region, i.e., the field of view. The modulated light is directed toward a light sensitive detector, producing a signal that can be analyzed by a processor to determine the velocity of the object. The velocity measurement subsystem is used to provide timing signals to TDI imaging detector 508.

Preferably, signal conditioning unit 505c comprises a programmable computing device, although an ASIC chip or a digital oscilloscope can also be used for this purpose. The frequency of the photodetector signal is measured, and the velocity of the object is computed as a function of that frequency. The velocity dependent signal is periodically delivered to a TDI detector timing control 505e to adjust the clock rate of TDI imaging detector 508. Those of ordinary skill in the art will recognize that the TDI detector clock rate is adjusted to match the velocity of the image of the object over the TDI detector to within a small tolerance selected to ensure that longitudinal image smearing in the output signal of the TDI detector is within acceptable limits. The velocity update rate must occur frequently enough to keep the clock frequency within the tolerance band as flow (object) velocity varies.

Beam splitter 503 has been employed to divert a portion of light from an object 502 to light sensitive detector 505b, and a portion of light from object 502a to TDI imaging detector 508. In the light path directed toward TDI imaging detector 508, there is a plurality of stacked dichroic filters 509, which separate light from object 502a into a plurality of wavelengths. One of lenses 507 is used to form an image of object 502a on TDI imaging detector 508.

The theory of operation of a TDI detector like that employed in system 510 is as follows. As objects travel through a flow tube 511 (FIG. 1) and pass through the volume imaged by the TDI detector, light from the objects forms images of the objects, and these images travel across the face of the TDI detector. The TDI detector preferably comprises a charge coupled device (CCD) array, which is specially designed to allow charge to be transferred on each clock cycle, in a row-by-row format, so that a given line of charge remains locked to, or synchronized with, a line in the image. The row of charge is clocked out of the array and into a memory when it reaches the bottom of the array. The intensity of each line of the signal produced by the TDI detector corresponding to an image of an object is integrated over time as the image and corresponding resulting signal propagate over the CCD array. This technique greatly improves the signal-to-noise ratio of the TDI detector compared to non-integrating type detectors—a feature of great benefit in a detector intended to respond to images from low-level fluorescence emission of an object. Proper operation of the TDI detector requires that the charge signal be clocked across the CCD array in synchronization with the rate at which the image of the object moves across the CCD array. An accurate clock signal to facilitate this synchronization can be provided by determining the velocity of the object, and the concepts disclosed herein use an accurate estimate of the object's velocity, and thus, of the velocity of the image as it moves over the CCD array of the TDI detector. A flow imaging system of this type is disclosed in commonly assigned U.S. Pat. No. 6,249,341, the complete disclosure, specification, and drawings of which are hereby specifically incorporated herein by reference.

Figure 1B:
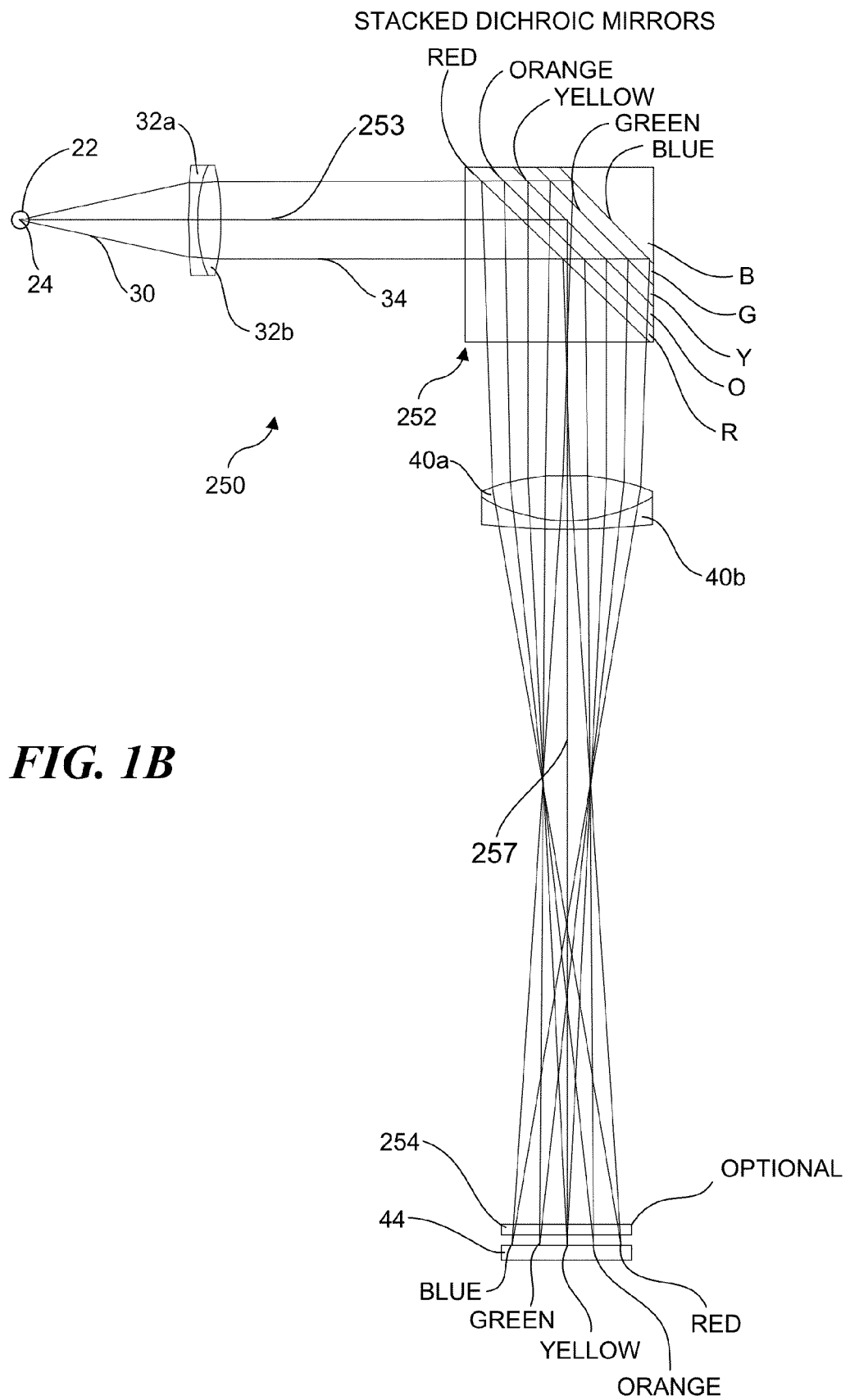
FIG. 1B is a plan view of an exemplary flow imaging system that employs a spectral dispersion component comprising a plurality of stacked dichroic filters employed to spectrally separate the light to simultaneously collect a plurality of images from an object in flow.
Figure 1C:
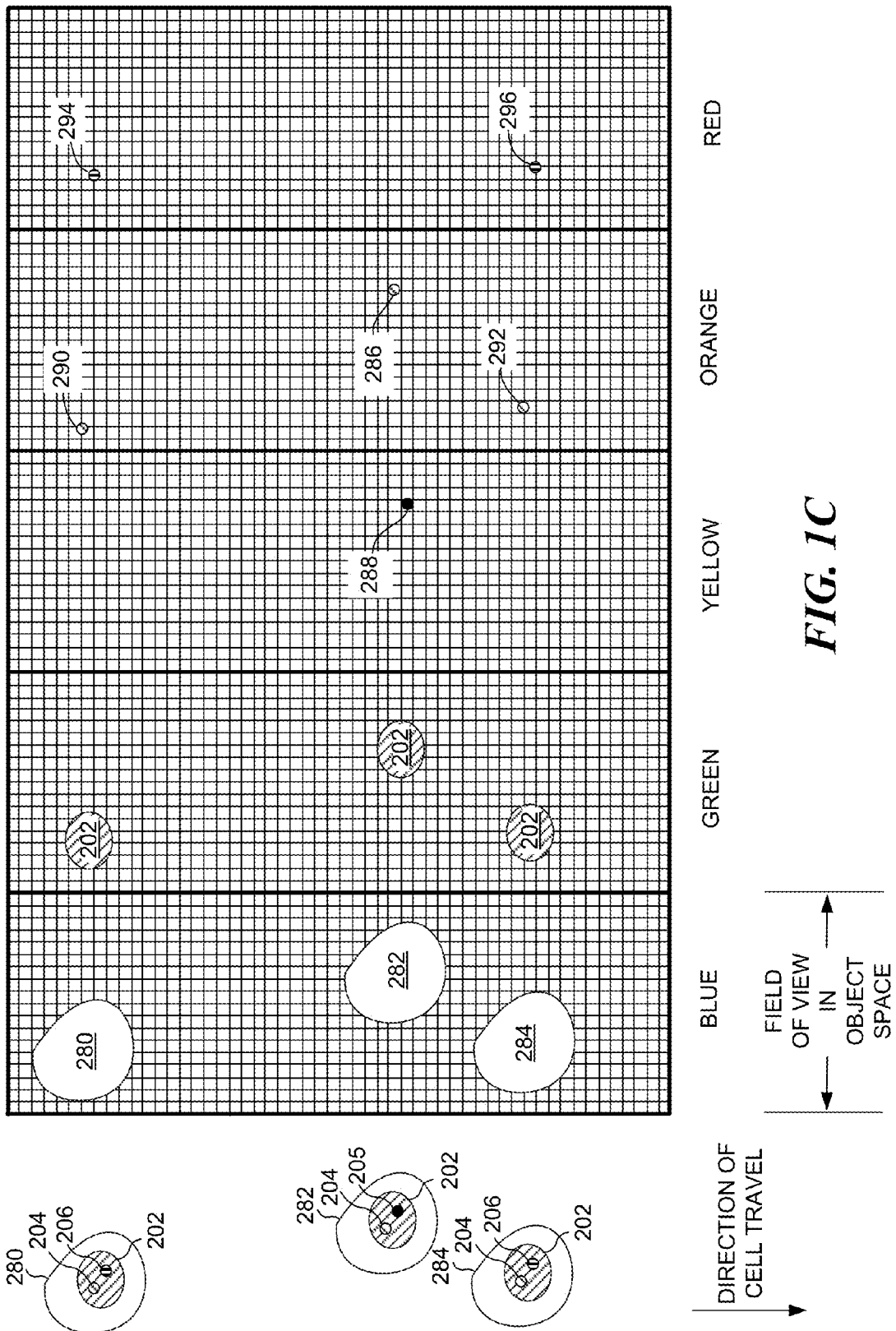
FIG. 1C illustrates an exemplary set of images projected onto the TDI detector when using the spectral dispersing filter system of the FIG. 1B.
Figure 2:
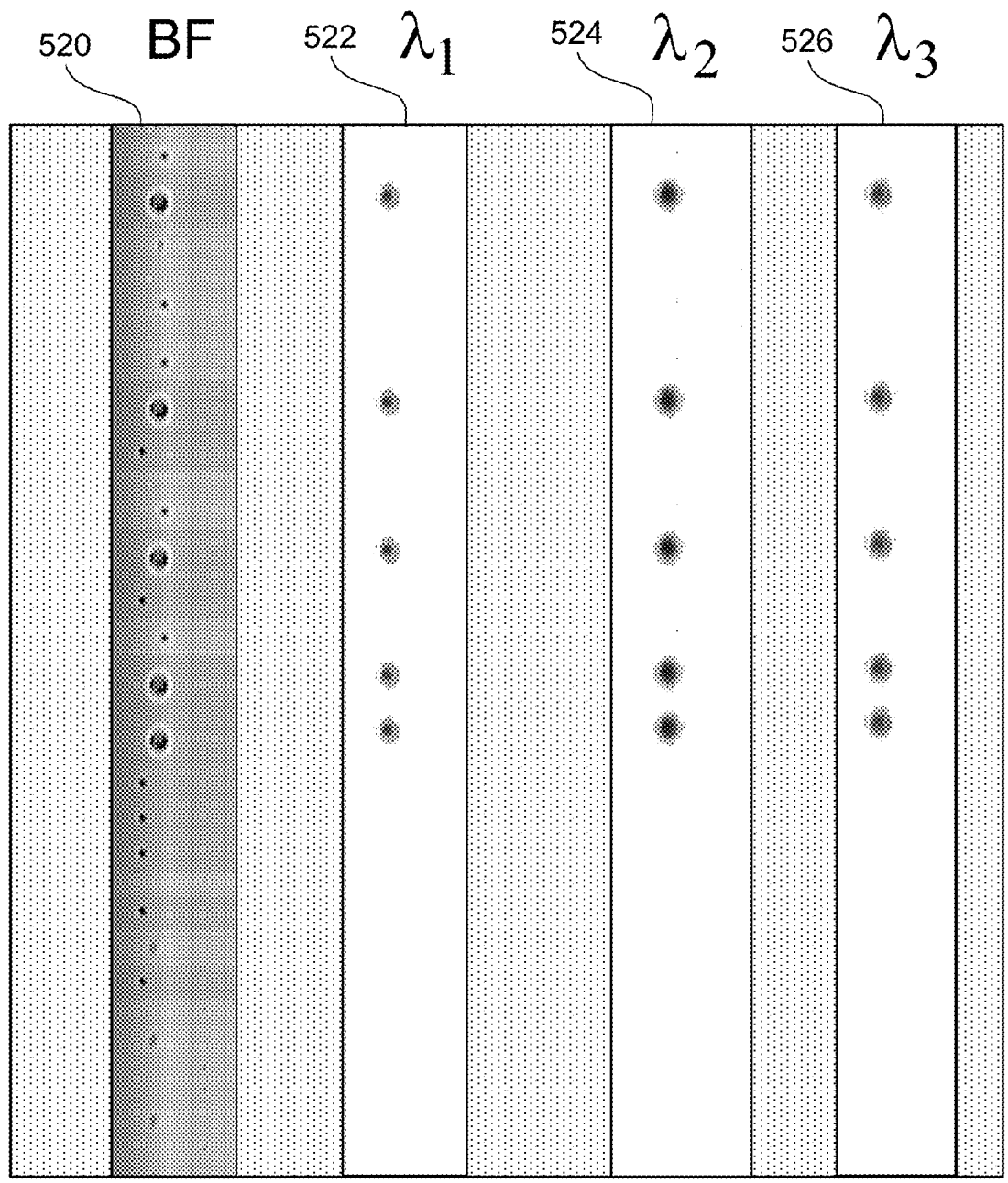
FIG. 2 is a pictorial representation of an image recorded by the flow imaging system of FIG. 1.

FIG. 2 is a pictorial representation of images produced by the flow imaging system of FIG. 1. A column 520, labeled "BF," includes images created by the absorption of light from light source 506 by spherical objects 502 entrained in fluid flow 504. The "BF" label refers to "bright field," a term derived from a method for creating contrast in an image whereby light is passed through a region and the absorption of light by objects in the region produces dark areas in the image. The background field is thus bright, while the objects are dark in this image. Thus, column 520 is the "bright field channel" It should be understood that the inclusion of a bright field image is exemplary, rather than limiting on the scope of the concepts disclosed herein. Preferably, the concepts disclosed herein utilize a combination of bright field images and fluorescent images, or of dark field images and fluorescent images.

The remaining three columns 522, 524, and 526 shown in FIG. 2 are respectively labeled "λ1," "λ2," and "λ3." These columns include images produced using light that has been emitted by an object entrained in the fluid flow. Preferably, such light is emitted through the process of fluorescence (as opposed to images produced using transmitted light). As those of ordinary skill in the art will recognize, fluorescence is the emission of light (or other electromagnetic radiation) by a substance that has been stimulated by the absorption of incident radiation. Generally, fluorescence persists only for as long as the stimulating radiation persists. Many substances (particularly fluorescent dyes) can be identified based on the spectrum of the light that is produced when they fluoresce. Columns 522, 524, and 526 are thus referred to as "fluorescence channels."

Additional exemplary flow imaging systems are disclosed in commonly assigned U.S. Pat. No. 6,211,955 and U.S. Pat. No. 6,608,682, the complete disclosure, specification, and drawings of which are hereby specifically incorporated herein by reference as background material. The imaging systems described above and in these two patents in detail, and incorporated herein by reference, have substantial advantages over more conventional systems employed for the acquisition of images of biological cell populations. These advantages arise from the use in several of the imaging systems of an optical dispersion system, in combination with a TDI detector that produces an output signal in response to the images of cells and other objects that are directed onto the TDI detector. Significantly, multiple images of a single object can be collected at one time. The image of each object can be spectrally decomposed to discriminate object characteristics by absorption, scatter, reflection, or emissions, using a common TDI detector for the analysis. Other systems include a plurality of detectors, each dedicated to a single spectral channel.

These imaging systems can be employed to determine morphological, photometric, and spectral characteristics of cells and other objects by measuring optical signals including light scatter, reflection, absorption, fluorescence, phosphorescence, luminescence, etc. Morphological parameters include area, perimeter, texture or spatial frequency content, centroid position, shape (i.e., round, elliptical, barbell-shaped, etc.), volume, and ratios of selected pairs (or subsets) of these parameters. Similar parameters can also be determined for the nuclei, cytoplasm, or other sub-compartments of cells with the concepts disclosed herein. Photometric measurements with the preferred imaging system enable the determination of nuclear optical density, cytoplasm optical density, background optical density, and ratios of selected pairs of these values. An object being imaged with the concepts disclosed herein can either be stimulated into fluorescence or phosphorescence to emit light, or may be luminescent, producing light without stimulation. In each case, the light from the object is imaged on the TDI detector to use the concepts disclosed herein to determine the presence and amplitude of the emitted light, the number of discrete positions in a cell or other object from which the light signal(s) originate(s), the relative placement of the signal sources, and the color (wavelength or waveband) of the light emitted at each position in the object.

Using a Multispectral Imaging System to Analyze Bodily Fluid for a Disease Condition As noted above, aspects of the concepts disclosed herein involve both the collection of multispectral images from a population of biological cells, and the analysis of the collected images to identify at least one photometric or morphological image feature that has been empirically determined to be associated with a disease condition. Thus, an aspect of the present disclosure relates to the use of both photometric and morphometric image features derived from multi-mode imagery of objects (e.g., cells) in flow to discriminate cell characteristics in populations of cells, to facilitate the detection of the presence of a disease condition. Discussed in more detail below are methods for analyzing cells in suspension or flow, which may be combined with comprehensive multi-spectral imaging to provide morphometric and photometric data to enable, for example, the quantization of characteristics exhibited by both normal cells and diseased cells, to facilitate the detection of diseased or abnormal cells indicative of a disease condition. Heretofore, such methods have not been feasible with standard microscopy and/or flow cytometry.

As noted above, a preferred flow imaging system (e.g., the ImageStream™ platform) can be used to simultaneously acquire multispectral images of cells in flow, to collect image data corresponding to bright field, dark field, and four channels of fluorescence. The ImageStream™ platform is a commercial embodiment based on the imaging systems described in detail above. In general, cells are hydrodynamically focused into a core stream and orthogonally illuminated for both dark field and fluorescence imaging. The cells are simultaneously trans-illuminated via a spectrally-limited source (e.g., filtered white light or a light emitting diode) for bright field imaging. Light is collected from the cells with an imaging objective lens and is projected on a CCD array. The optical system has a numeric aperture of 0.75 and the CCD pixel size in object space is $0.5\mu^2$, enabling high resolution imaging at event rates of approximately 100 cells per second. Each pixel is digitized with 10 bits of intensity resolution in this example, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object. It should be understood that while the ImageStream™ platform represents a particularly preferred flow imaging system for acquiring image data in accord with the concepts disclosed herein, the ImageStream™ platform is intended to represent an exemplary imaging system, rather than limiting the concepts disclosed. Any imaging instrument capable of collecting images of a population of biological cells sufficient to enable the image analysis described in greater detail below to be achieved can be implemented in accord with the concepts presented herein.

Referring again to the preferred imaging system, the ImageStream™ platform, prior to projection on the CCD, the light is passed through a spectral decomposition optical system that directs different spectral bands to different lateral positions across the detector (such spectral decomposition is discussed in detail above in connection with the description of the various preferred embodiments of imaging systems). With this technique, an image is optically decomposed into a set of a plurality of sub-images (preferably 6 sub-images, including: bright field, dark field, and four different fluorescent images), each sub-image corresponding to a different spectral (i.e., color) component and spatially isolated from the remaining sub-images. This process facilitates identification and quantization of signals within the cell by physically separating on the detector signals that may originate from overlapping regions of the cell. Spectral decomposition also enables multimode imaging, i.e., the simultaneous detection of bright field, dark field, and multiple colors of fluorescence.

The process of spectral decomposition occurs during the image formation process, rather than via digital image processing of a conventional composite image.

The CCD may be operated using TDI to preserve sensitivity and image quality even with fast relative movement between the detector and the objects being imaged. As with any CCD, image photons are converted to photo charges in an array of pixels. However, in TDI operation, the photo charges are continuously shifted from pixel to pixel down the detector, parallel to the axis of flow. If the photo charge shift rate is synchronized with the velocity of the image of the cell, the effect is similar to physically panning a camera. Image streaking is avoided despite signal integration times that are orders of magnitude longer than in conventional flow cytometry. For example, an instrument may operate at a continuous data rate of approximately 30 mega pixels per second and integrate signals from each object for 10 milliseconds, enabling the detection of even faint fluorescent probes within cell images to be acquired at relatively high speed. Careful attention to pump and fluidic system design to achieve highly laminar, non-pulsatile flow eliminates any cell rotation or lateral translation on the time scale of the imaging process (see, e.g., U.S. Pat. No. 6,532,061).

A real-time algorithm analyzes every pixel read from the CCD to detect the presence of object images and calculate a number of basic morphometric and photometric image features, which can be used as criteria for data storage. Data files encompassing 10,000-20,000 cells are typically about 100 MB in size and, therefore, can be stored and analyzed using standard personal computers. The TDI readout process operates continuously without any "dead time," which means every cell can be imaged and the coincidental imaging of two or more cells at a time either in contact or not, presents no barrier to data acquisition.

Such an imaging system can be employed to determine morphological, photometric, and spectral characteristics of cells and other objects by measuring optical signals, including light scatter, reflection, absorption, fluorescence, phosphorescence, luminescence, etc. As used herein, morphological parameters (i.e., morphometrics) may be basic (e.g., nuclear shape) or may be complex (e.g., identifying cytoplasm size as the difference between cell size and nuclear size). For example, morphological parameters may include nuclear area, perimeter, texture or spatial frequency content, centroid position, shape (i.e., round, elliptical, barbell-shaped, etc.), volume, and ratios of selected pairs of these parameters. Morphological parameters of cells may also include cytoplasm size, texture or spatial frequency content, volume, and the like. As used herein, photometric measurements with the aforementioned imaging system can enable the determination of nuclear optical density, cytoplasm optical density, background optical density, and the ratios of selected pairs of these values. An object being imaged can be stimulated into fluorescence or phosphorescence to emit light, or may be luminescent, wherein light is produced by the object without stimulation. In each case, the light from the object may be imaged on a TDI detector of the imaging system to determine the presence and amplitude of the emitted light, the number of discrete positions in a cell or other object from which the light signal(s) originate(s), the relative placement of the signal sources, and the color (wavelength or waveband) of the light emitted at each position in the object.

The present disclosure provides methods of using both photometric and morphometric image features derived from multi-mode imagery of objects in flow. Such methods can be employed as a cell analyzer to determine if one or more image features corresponding to a disease condition is present in the population of cells imaged. As noted above, certain image features can be indicative of the cellular abnormality associated with a disease condition, or image features can be indicative of a change in a ratio of subpopulations present in the population of the cells imaged, where the change in ratio is indicative of a disease condition. Preferably the population of cells is imaged while entrained in a fluid flowing through an imaging system. As used herein, gating refers to a subset of data relating to photometric or morphometric imaging. For example, a gate may be a numerical or graphical boundary of a subset of data that can be used to define the characteristics of particles to be further analyzed. Here, gates have been defined, for example, as a plot boundary that encompasses "in focus" cells, or sperm cells with tails, or sperm cells without tails, or cells other than sperm cells, or sperm cell aggregates, or cell debris. Further, backgating may be a subset of the subset data. For example, a forward scatter versus a side scatter plot in combination with a histogram from an additional image feature may be used to backgate a subset of cells within the initial subset of cells.

In using an imaging system as described herein, it should be made clear that a separate light source is not required to produce an image of the object (cell), if the object is luminescent (i.e., if the object produces light). However, many of the applications of an imaging system as described herein will require that one or more light sources be used to provide light that is incident on the object being imaged. A person having ordinary skill in the art will know that the locations of the light sources substantially affect the interaction of the incident light with the object and the kind of information that can be obtained from the images using a detector.

In addition to imaging an object with the light that is incident on it, a light source can also be used to stimulate emission of light from the object. For example, a cell having been contacted with a probe conjugated to a fluorochrome (e.g., such as FITC, PE, APC, Cy3, Cy5, or Cy5.5) will fluoresce when excited by light, producing a corresponding characteristic emission spectra from any excited fluorochrome probe that can be imaged on a TDI detector. Light sources may alternatively be used for causing the excitation of fluorochrome probes on an object, enabling a TDI detector to image fluorescent spots produced by the probes on the TDI detector at different locations as a result of the spectral dispersion of the light from the object that is provided by a prism. The disposition of these fluorescent spots on the TDI detector surface will depend upon their emission spectra and their location in the object.

Each light source may produce light that can either be coherent, non-coherent, broadband, or narrowband light, depending upon the application of the imaging system desired. Thus, a tungsten filament light source can be used for applications in which a narrowband light source is not required. For applications such as stimulating the emission of fluorescence from probes, narrowband laser light is preferred, since it also enables a spectrally decomposed, non-distorted image of the object to be produced from light scattered by the object. This scattered light image will be separately resolved from the fluorescent spots produced on a TDI detector, so long as the emission spectra of any of the spots are at different wavelengths than the wavelength of the laser light. The light source can be either of the continuous wave (CW) or pulsed type, such as a pulsed laser. If a pulsed type illumination source is employed, the extended integration period associated with TDI detection can enable the integration of signals from multiple pulses. Furthermore, it is not necessary for the light to be pulsed in synchronization with the TDI detector.

Particularly for use in collecting image data for cell populations found in bodily fluids such as blood, it can be desirable to employ a 360 nm UV laser as a light source, and to optimize the optical system of the imaging system for diffraction-limited imaging performance in the 400-460 nm (DAPI emission) spectral band.

In embodiments consistent with the disclosure herein, it is to be understood that relative movement exists between the object being imaged and the imaging system. In most cases, it will be more convenient to move the object than to move the imaging system. It is also contemplated that in some cases, the object may remain stationary and the imaging system move relative to it. As a further alternative, both the imaging system and the object may be in motion, which movement may be in different directions and/or at different rates.

Exemplary Imaging System and Detector

While the principles of preferred imaging systems have been discussed above, the following provides a more detailed description of an exemplary imaging system, and an exemplary detector, in order to describe how the imaging optics and detector cooperate to achieve the simultaneous collection of a plurality of images.

The following imaging system employs a spectral dispersion filter assembly that does not convolve the acquired images with the emission spectra of the light forming the images, thereby eliminating the need for deconvolution of the emission spectra from the image. FIG. 1B illustrates a non-distorting spectral dispersion system 250 that employs a five color stacked wedge spectral dispersing filter assembly 252.

In FIG. 1B (which is a plan view), a fluid flow 22 entrains an object 24 (such as a cell, but alternatively, a small particle) and carries the object through the imaging system. The direction of the fluid flow in FIG. 1B is into (or out of) the drawing sheet. Light 30 from object 24 passes through collection lenses 32a and 32b that collect the light, producing collected light 253, which is approximately focused at infinity, i.e. the rays of collected light from collection lens 32b are generally parallel. Collected light 253 enters spectral dispersing filter assembly 252, which disperses the light, producing dispersed light 257. The dispersed light then enters imaging lenses 40a and 40b, which focuses light 257 onto a TDI detector 44.

The spectral dispersing filter assembly splits the light into a plurality of light beams having different bandwidths. Each light beam thus produced is directed at a different nominal angle so as to fall upon a different region of TDI detector 44. The nominal angular separation between each bandwidth produced by the spectral dispersing filter assembly 252 exceeds the field angle of the imaging system in object space thereby preventing overlap of the field images of various bandwidths on the detector.

Spectral dispersing filter assembly 252 comprises a plurality of stacked dichroic wedge filters, including a red dichroic filter R, an orange dichroic filter O, a yellow dichroic filter Y, a green dichroic filter G, and a blue dichroic filter B. Red dichroic filter R is placed in the path of collected light 34, oriented at an angle of approximately 44.0° relative to an optic axis 253 of collection lenses 32a and 32b. Light of red wavelengths and above, i.e., >640 nm, is reflected from the surface of red dichroic filter R at a nominal angle of 1°, measured counter-clockwise from a vertical optic axis 257. The light reflected by red dichroic filter R leaves spectral dispersing filter assembly 252 and passes through imaging lenses 40a and 40b, which cause the light to be imaged onto a red light receiving region of TDI detector 44, which is disposed toward the right end of the TDI detector, as shown in FIG. 1B.

Orange dichroic filter O is disposed a short distance behind red dichroic filter R and is oriented at an angle of 44.5 degrees with respect to optic axis 253. Light of orange wavelengths and greater, i.e., >610 nm, is reflected by orange dichroic filter O at a nominal angle of 0.5° with respect to vertical optic axis 257. Because the portion of collected light 34 comprising wavelengths longer than 640 nm was already reflected by red dichroic filter R, the light reflected from the surface of orange dichroic filter O is effectively bandpassed in the orange colored region between 610 nm and 640 nm. This light travels at a nominal angle of 0.5° from vertical optic axis 257, and is imaged by imaging lenses 40a and 40b so as to fall onto an orange light receiving region disposed toward the right hand side of TDI detector 44 between a center region of the TDI detector and the red light receiving region, again as shown in FIG. 1B.

Yellow dichroic filter Y is disposed a short distance behind orange dichroic filter O and is oriented at an angle of 45° with respect to optic axis 253. Light of yellow wavelengths, i.e., 560 nm and longer, is reflected from yellow dichroic filter Y at a nominal angle of 0.0° with respect to vertical optic axis 257. Wavelengths of light reflected by yellow dichroic filter Y are effectively bandpassed in the yellow region between 560 nm and 610 nm and are imaged by imaging lenses 40a and 40b near vertical optic axis 257 so as to fall on a yellow light receiving region toward the center of TDI detector 44.

In a manner similar to dichroic filters R, O, and Y, dichroic filters G and B are configured and oriented so as to image green and blue light wavebands onto respective green and blue light receiving regions of TDI detector 44, which are disposed toward the left-hand side of the TDI detector. By stacking the dichroic filters at different predefined angles, spectral dispersing filter assembly 252 collectively works to focus light within predefined wavebands of the light spectrum onto predefined regions of TDI detector 44.

The wedge shape of the dichroic filters in the preceding discussion allows the filters to be placed in near contact, in contact or possibly cemented together to form the spectral dispersing filter assembly 252. The angle of the wedge shape fabricated into the substrate for the dichroic filter allows easy assembly of the spectral dispersing filter assembly 252, forming a monolithic structure in which the wedge-shaped substrate is sandwiched between adjacent dichroic filters. If the filters are in contact with each other or cemented together, the composition of the materials that determine the spectral performance of the filter may be different from those which are not in contact. Those of ordinary skill in the art will appreciate that flat, non wedge-shaped substrates could be used to fabricate the spectral dispersing filter assembly 252. In this case another means such as mechanically mounting the filters could be used to maintain the angular relationships between the filters.

In addition to the foregoing configuration, non-distorting spectral dispersion system 250 may optionally include a detector filter assembly 254 to further attenuate undesired signals in each of the light beams, depending upon the amount of rejection required for out-of-band signals. In the embodiment shown in FIG. 1B, light may pass through each dichroic filter in the spectral dispersing filter assembly 252 twice before exiting the spectral dispersing filter assembly 252. This condition will further attenuate out-of-band signals, but will also attenuate in-band signals.

The foregoing description illustrates the use of a five color system. Those skilled in the art will appreciate that a spectral dispersing component with more or fewer filters may be used in these configurations in order to construct a system covering a wider or a narrower spectral region, or different passbands within a given spectral region. Likewise, those skilled in the art will appreciate that the spectral resolution of the present invention may be increased or decreased by appropriately choosing the number and spectral characteristics of the dichroic and or bandpass filters that are used. Furthermore, those skilled in the art will appreciate that the angles or orientation of the filters may be adjusted to direct light of a given bandwidth onto any desired point on the TDI detector. In addition, there is no need to focus the light in increasing or decreasing order by wavelength. For example, in fluorescence imaging applications, one may wish to create more spatial separation on the TDI detector between the excitation and emission wavelengths by changing the angles at which the filters corresponding to those wavelengths are oriented with respect to the optic axes of the system. Finally, it will be clear to those skilled in the art that dispersion of the collected light may be performed on the basis of non-spectral characteristics, including angle, position, polarization, phase, or other optical properties.

FIG. 1C illustrates the distribution of images on TDI detector 44 corresponding to imaging a plurality of cells 280-284 using non-distorting spectral dispersion system 250. Significantly, the field angle of system 250 is orthogonal to flow in object space, such that the individual images are laterally dispersed across detector 44 (as indicated on FIG. 1C), substantially orthogonal to a direction of a motion of the respective images across the TDI detector (i.e., the object moves vertically across the detector, and the plurality of images are dispersed horizontally across the detector).

In this particular configuration, the field angle in object space is less than +/−0.25°. Those skilled in the art will appreciate that the field angle can be made larger or smaller. To the extent that the field angle is made larger, for example, to image cells over a wider region on a slide or in a broad flat flow, the field angle at the detector will increase in proportion to the number of colors used. FIG. 1C illustrates the image projected onto the detector when three cells 280, 282 and 284 are flowing through the field of view. Light scatter images of cells 280, 282, and 284 are seen on the left hand side of the detector denoted as the BLUE area. Images of cell nuclei 202 stained with a green fluorescent dye are seen in the GREEN area of the detector. Three differently-colored genetic probes 204, 205, and 206 are also employed for the analysis of the sex chromosomes within the cells. Probe 204 stains the X chromosome with an orange fluorescing dye, probe 205 stains the Y chromosome with yellow fluorescing dye, and probe 206 stains the inactive X chromosome in female cells with a red fluorescing dye. Cell 282 is imaged onto the detector as shown in FIG. 1C. An image 286 of probe 204 from cell 282 is seen in the ORANGE area of the detector. Likewise an image 288 of probe 205 from cell 282 is seen in the YELLOW area of the detector. The signal on the detector is processed to determine the existence and position of these images on the detector to determine that cell 282 is a male cell. In a similar manner, cells 280 and 284 contain probes 204 and 206, which create images 290 and 292 in the ORANGE area of the detector, and images 294 and 296 in the RED area of the detector, indicating that these cells are female, respectively.

Exemplary High Level Method Steps

FIG. 3 is a flow chart 400 schematically illustrating exemplary steps that can be used to analyze a population of cells based on images of the cell population, in order to identify a disease condition. In a particularly preferred embodiment, the cell population is obtained from a bodily fluid, such as blood. In a block 402, an imaging system, such as the exemplary imaging system described above in detail, is used to collect image data from a first population of biological cells where a disease condition is known to be present. In a block 404 at least one photometric or morphometric image feature associated with the disease condition is identified. In the empirical study described below, two distinctly different types of image features were developed. One type of image feature relates to identifying a photometric and/or morphometric difference between healthy cells and diseased cells. One technique in identifying such an image feature is to label carcinoma cells with a fluorescent label, and compare images of fluorescently labeled carcinoma cells with images of healthy cells, to identify a plurality of photometric and morphometric image features associated with the carcinoma cells. As will be described in greater detail below, such image features include differences in the average nucleus size between healthy cells and carcinoma cells, and differences in fluorescent images of healthy cells and carcinoma cells. These differences can be quantified based on processing the image data for the population of cells, to identify images that are more likely to be images of carcinoma cells, and to identify images that are more likely to be images of healthy cells.

Another type of image feature relates to identifying some difference between subpopulations present in a cellular population absent the disease condition, and subpopulations present in a cellular population during the disease condition. For example, CLL is a disease condition where the number of lymphocytes in blood increases relative to the numbers of other blood cell types. Thus, a change in the ratio of lymphocytes to other blood cell types can be indicative of a disease condition.

Once a photometric and/or morphometric image feature associated with the disease condition is identified, image data are collected from a second population of cells, in which it is not known whether the disease condition exists or not. In a block 408 image data are collected for the second population of cells, and then the image data are analyzed for the presence of the previously identified image feature, to determine whether the disease condition is present in the second population of cells.

Significantly, where the imaging systems described above are used to collect the image data from a population of cells, the image data can be collected quite rapidly. In general, the analysis (i.e., analyzing the collected image data to either initially identify an image feature or to determine the presence of a previously identified image feature in a population of cells) will be performed off-line, i.e., after the collection of the image data. Current implementations of imaging processing software are capable of analyzing a relatively large population of cells (i.e., tens of thousands of cells) within tens of minutes using readily available personal computers. However, it should be recognized that as more powerful computing systems are developed and become readily available, it may become possible to analyze the image data in real-time. Thus, off-line processing of the image data is intended to be exemplary, rather than limiting, and it is contemplated that real-time processing of the image data is an alternative.

Where the image feature relates to some photometric and/or morphometric difference between a healthy cell and a diseased cell, before using an imaging instrument to collect image data on the first population of cells (the population known to be associated with the disease condition), it can be desirable to label either the diseased cells or the healthy cells, particularly where the first population includes a mixture of both diseased and healthy cells. This approach facilitates separating the collected image data into images corresponding to diseased cells and images corresponding to healthy cells, to facilitate identification of photometric and/or morphometric image features that can be used to distinguish the two. It should be recognized however, that the first population could include only diseased cells, and that if the image data of the first population is compared with image data of a cell population known to include only healthy cells, the photometric and/or morphometric image features that can be used to distinguish the diseased cells from the healthy cells can readily be identified.

Where the image feature relates to some photometric and/or morphometric difference between subpopulations present in a cellular population absent the disease condition, and subpopulations present in a cellular population associated with disease condition, image data corresponding to the subpopulations present in a healthy cellular population must be provided before the image data corresponding to the first population of cells (the population known to be associated with the disease condition) can be analyzed to identify some photometric and/or morphometric difference between the subpopulations present in the healthy cellular population, and the subpopulations present in the cellular population having the disease condition.

While not strictly required, in a working embodiment of the techniques described herein, additional processing was implemented to reduce crosstalk and spatial resolution for the multi-channel imaging. The crosstalk reduction processing implemented is described in commonly assigned U.S. Pat. No. 6,763,149, the specification, disclosure and the drawings of which are hereby specifically incorporated herein by reference as background material. Those of ordinary skill in the art will recognize that other types of crosstalk reduction techniques could alternatively be implemented.

Identification of Exemplary Photometric and Morphometric Disease Condition Features In the context of the present disclosure, the multi-spectral imaging flow cytometer described above employs UV excitation capabilities and algorithms to quantitate DNA content and nuclear morphology, for the purpose of detecting and monitoring disease conditions, such as chronic lymphocytic leukemia. In addition to employing a flow imaging instrument including a 360 nm UV laser and an optical system optimized for diffraction-limited imaging performance in the 400-460 nm (DAPI emission) spectral band, an imaging processing system is employed to process the image data. A personal computer executing image processing software represents an exemplary imaging processing system. The imaging processing software incorporates algorithms enabling photometric and/or morphometric properties of cells to be determined based on images of the cells. Exemplary algorithms include masking algorithms, algorithms that define nuclear morphology, algorithms for the quantization of cell cycle histograms, algorithms for analyzing DNA content, algorithms for analyzing heterochromaticity, algorithms for analyzing N/C ratio, algorithms for analyzing granularity, algorithms for analyzing CD45 expression, and algorithms for analyzing other parameters. In addition, the imaging processing software incorporates an algorithm referred to as a classifier, a software based analysis tool that is configured to evaluate a sample population of cells to determine if any disease condition image features are present. For determining the presence of cancer cells, the classifier will analyze the images of the sample population for images having photometric and/or morphometric properties corresponding to previously identified photometric and/or morphometric properties associated with cancer cells.

For samples of cell populations being analyzed to detect CLL, the classifier will analyze the images of the sample population to separate the images into different cellular subpopulations (based on different types of blood cells), and determine if the ratios of the subpopulations indicates the presence of CLL (for example, because of a higher than normal amount of lymphocytes). Preferably, the classifier configured to detect CLL will separate blood cells into the following subpopulations: lymphocytes, monocytes, basophils, neutrophils, and eosinophils. The classifier configured to detect CLL will be based on empirical data from healthy patients and from patients with CLL. Classifier profiles for CLL can be improved by collecting and comparing classifier data for a variety of patients with the same diagnosis. Preferably, large (10,000 to 20,000-cell) data sets from each patient will be collected to assess the existence and diagnostic significance of CLL cell subpopulations for classifier optimization. Such an optimized classifier can then be used to monitor patient treatment response and assess residual disease after treatment.

Significantly, for detection of epithelial cell carcinomas, high rates of data acquisition is required. Such cells have been reported to range from 1 cell in 100,000 peripheral blood leukocytes to 1 cell in 1,000,000 peripheral blood leukocytes. The ImageStream™ cytometer and IDEAS™ analytical software package discussed above are ideally suited for this application. Imagery from peripheral blood leukocytes can be obtained in the absence of artifacts typical of preparing blood films. Large cell numbers (in the tens and hundreds of thousands) can be accumulated per sample, providing greater confidence in the analysis of subpopulations. Immunofluorescent staining with accepted markers (CD5, CDI9, etc.) can easily be correlated with morphology. The quantitative cell classifiers eliminate the subjectivity of human evaluation, giving comparisons between patients a degree of confidence previously unattainable. Longitudinal studies will also benefit greatly by the quantitative analysis, and the ability to digitally store and retrieve large numbers of cellular image files, particularly as compared to prior art techniques for the retrieval of microscope slides and/or digital photographs of relatively small numbers of cells.

Discrimination of Morphological Features Using Fluorescence-Based Methodologies

A technology employed in detection of cancer cells in a bodily fluid based on image data of a population of cells from the bodily fluid was the development of preliminary absorbance and fluorescence staining protocols for simultaneous morphological analysis of bright field and fluorescence imagery.

Initially, investigations considered the simultaneous use of chromogenic stains and fluorescent dyes. The ability of the imaging system discussed above to produce bright field imagery, as well as multiple colors of fluorescence imagery of each cell, raised the possibility of simultaneously employing both traditional chromogenic stains and fluorescent dyes for analysis. However, because chromogenic stains do not normally penetrate cell membranes of viable cells, and because the optical systems discussed above are able to collect laser side scatter imagery, it was determined that much of the information on cell granularity that was traditionally acquired via stains, such as Eosin, could be obtained using laser side scatter imagery, without the need for cell staining Numerous cell-permeant fluorescent dyes offer nuclear morphology without the need for fixing and chromogenic staining. Based on these considerations, it was determined that fluorescence-based alternatives for discrimination of morphological image features provide a better approach than traditional staining methodologies.

The primary fluorescence-based alternatives to chromogenic stains useful in conjunction with the optical systems discussed above are fluorescent DNA binding dyes. A wide variety of such dyes are excitable at 488 nm, including several SYTO dyes (Molecular Probes), DRAQ5 (BioStatus), 7-AAD, Propidium Iodide (PI), and others. These dyes are alternatives to chromogenic nuclear stains such as Toluidine Blue, Methyl Green, Crystal Violet, Nuclear Fast Red, Carmalum, Celestine Blue, and Hematoxylin. A fluorescent DNA binding dye is generally included in assay protocols developed for use with the optical systems described above, for the purposes of defining the shape and boundaries of the nucleus, its area, its texture (analogous to heterochromaticity), as well as to provide DNA content information.

Figures 4, 5:
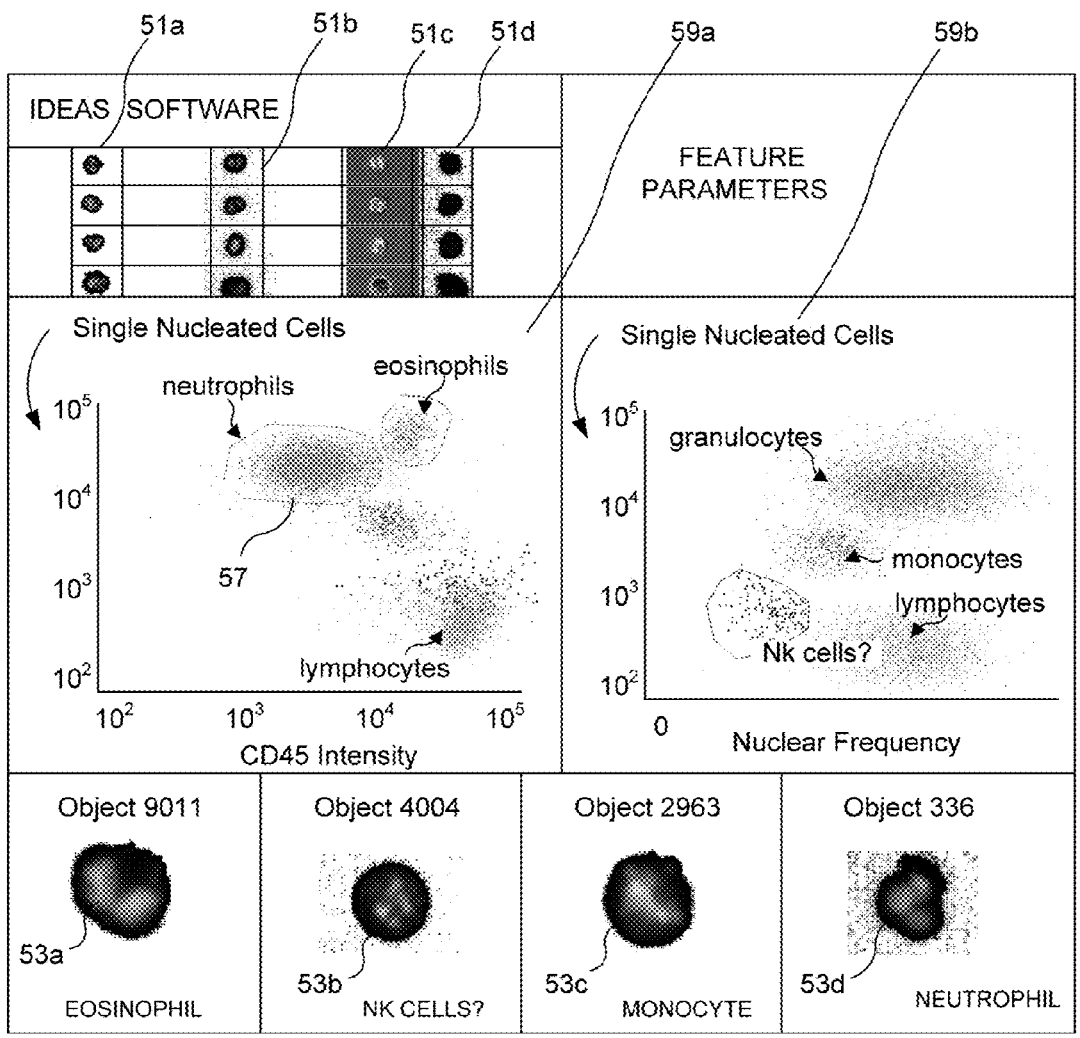
FIG. 4 is an exemplary graphical user interface used to implement the method steps of FIG. 3.
FIG. 5 is an exemplary graphical user interface used to implement the method steps of FIG. 3 as applied to the analysis of human peripheral blood.

IDEAS™, the software image analysis program discussed above, enables evaluation of combinations of image features from different images of the same cell, in order to expand the utility of the fluorescence nuclear image. For example, the nuclear image mask can be subtracted from the bright field image mask (which covers the entire cell) as a means for generating a mask that includes only the cytoplasmic region. Once defined, the cytoplasmic mask can be used to calculate the cytoplasmic area, the N/C ratio, the relative fluorescence intensity of probes in the cytoplasm and nucleus, etc., via an intuitive "Feature Manager." An example of a Feature Manager session for the definition of the N/C ratio is shown in FIG. 4. Basic image features associated with any cell image are selected from a list and combined algebraically using a simple expression builder.

Measurement of Photometric and Morphometric Parameters

In an exemplary implementation of the concepts disclosed herein, ImageStream™ data analysis and cell classification are performed post-acquisition using the IDEAS™ software package. An annotated IDEAS™ software screen capture of an analysis of human peripheral blood is shown in FIG. 5. The IDEAS™ software enables the visualization and photometric/morphometric analysis of data files containing imagery from tens of thousands of cells, thereby combining quantitative image analysis with the statistical power of flow cytometry.

The exemplary screen shot of FIG. 5 includes images and quantitative data from 20,000 human peripheral blood mononuclear cells. Whole blood was treated with an erythrocyte lysing agent, and the cells were labeled with an anti-CD45-PerCP mAb (red) and a DNA binding dye (green). Each cell was imaged in fluorescence using the FL1 and FL4 spectral bands, as well as dark field and bright field. Images of a plurality of cells in a dark field channel 51a, a green fluorescent channel 51b, a bright field channel 51c, and a red fluorescent channel 51d can readily be identified in this Figure. Such a thumbnail image gallery (in the upper left of the interface) enables the "list mode" inspection of any population of cells. Cell imagery can be pseudo-colored and superimposed for visualization in the image gallery or enlarged, as shown at the bottom of the interface, for four different cell types (eosinophils 53a, NK cells 53b, monocytes 53c, and neutrophils 53d).

The software also enables one- and two-dimensional plotting of image features calculated from the imagery. Dots 55 that represent cells in the two-dimensional plots can be "clicked" to view the associated imagery in the gallery. The reverse is true as well. Cell imagery can be selected to highlight the corresponding dot in every plot in which that cell appears. In addition, gates 57 can be drawn on the plots to define subpopulations, which can then be inspected in the gallery using a "virtual cell sort" functionality. Any image feature calculated from the imagery or defined by the user (i.e., selected from a list of basic and automatically combined algebraically using a simple expression builder) can be plotted. A dot plot 59a (displayed at the center left of FIG. 5) shows the clustering resulting from an analysis of CD45 expression (x-axis) versus a dark field granularity metric (y-axis), which is similar to side-scatter intensity measured in conventional flow cytometry. Plot 59a reveals lymphocytes (green in a full color image), monocytes (red in a full color image), neutrophils (turquoise in a full color image), and eosinophils (orange in a full color image). A dot plot 59b (displayed at the center right of FIG. 5) substitutes a nuclear texture parameter, "nuclear frequency" for CD45 expression on the x-axis, revealing a putative NK cell population (purple in a full color image). Back-displaying the purple population on the left dot plot reveals that this population has the same mean CD45 expression as the lymphocyte population (green on a full color image). The frequency parameter is one member of the morphologic and photometric image feature set that was developed and incorporated into the IDEAS™ software package. Table 1 below provides an exemplary listing of exemplary photometric and morphometric definitions that can be identified for every image (or subpopulation, as appropriate). It should be recognized that FIG. 5 has been modified to facilitate its reproduction. As a full-color image, the background of each frame including a cell is black, and the background for each dot plot is black, to facilitate visualization of the cells and data.

TABLE 1

Morphometric and Photometric Definitions

| Image Features | Description of Parameters for Each Image (6 per object) |
|---|---|
| Area | Area of mask in pixels |
| Aspect Ratio | Aspect ratio of mask |
| Aspect Ratio Intensity | Intensity-weighted aspect ratio of mask |
| Background Mean Intensity | Mean intensity of pixels outside of mask |
| Background StdDev Intensity | Standard deviation of intensity of pixels outside of mask |
| Centroid X | Centroid of mask in horizontal axis |
| Centroid X Intensity | Intensity-weighted centroid of mask in horizontal axis |
| Centroid Y | Centroid of mask in vertical axis |
| Centroid Y Intensity | Intensity-weighted centroid of mask in vertical axis |
| Combined Mask Intensity | Total intensity of image using logical "OR" of all six image masks |
| Frequency | Variance of intensity of pixels within mask |
| Gradient Max | Maximum intensity gradient of pixels within mask |
| Gradient RMS | RMS of intensity gradient of pixels within mask |
| Intensity | Background-corrected sum of pixel intensities within mask |
| Major Axis | Major axis of mask in pixels |
| Major Axis Intensity | Intensity-weighted major axis of mask in pixels |
| Mean Intensity | Total Intensity of image divided by area of mask |
| Minimum Intensity | Minimum pixel intensity within mask |

TABLE 1-continued

Morphometric and Photometric Definitions

| Image Features | Description of Parameters for Each Image (6 per object) |
| --- | --- |
| *Minor Axis* | *Minor axis of mask in pixels* |
| *Minor Axis Intensity* | *Intensity-weighted minor axis of mask in pixels* |
| Object Rotation Angle | Angle of major axis relative to axis of flow |
| Object Rotation Angle Intensity | Angle of intensity-weighted major axis relative to axis of flow |
| Peak Intensity | Maximum pixel intensity within mask |
| *Perimeter* | *Number of edge pixels in mask* |
| Spot Large Max | Maximum pixel intensity within large bright spots |
| Spot Large Total | Sum of pixel intensities within large bright spots |
| Spot Medium Max | Maximum pixel intensity within medium-sized bright spots |
| Spot Medium Total | Sum of pixel intensities within medium-sized bright spots |
| Spot Raw Max | Un-normalized maximum pixel intensity within large bright spots |
| Spot Raw Total | Sum of un-normalized pixel intensities within large bright spots |
| Spot Small Max | Maximum pixel intensity within small bright spots |
| Spot Small Total | Sum of pixel intensities within small bright spots |
| Total Intensity | Sum of pixel intensities within mask |
| *Spot Count* | *Number of spots detected in image* |
| Combined Mask Area | Area of logical 'OR' of all six image masks in pixels |
| Flow Speed | Camera line readout rate in Hertz at time object was imaged |
| Object Number | Unique object number |
| *Similarity* | *Pixel intensity correlation between two images of the same object* |
| *User-Defined Features* | *Any algebraic combination of imagery and masks* |
| *User-Defined Masks* | *Erode, dilate, threshold, Boolean combinations* |
| User-Defined Populations | Any Boolean combination of defined populations |

Image features that quantitate morphology are shown in italics in Table 1. Each image feature is automatically calculated for all six types of images (dark field, bright field, and four fluorescent images, that are simultaneously captured) for each cell, when an image data set is loaded into the software.

Over 35 image features are calculated per image, which amounts to over 200 image features per cell in assays that employ all six images, not including user-defined image features. Each cell is also assigned a unique serial number and time stamp, enabling kinetic studies over cell populations.

Selection of a Photometric/Morphometric Image Features for Carcinoma Cells

It was initially proposed that bladder epithelial cells would be used to investigate morphometric differences between normal and epithelial carcinoma cells. However, the initial samples of bladder washings that were analyzed revealed that the cell number per sample was highly variable, and generally too low to be practical for use in the ImageStream™ instrument. Mammary epithelial cells were therefore used in place of bladder cells. Mammary cells were chosen because normal, primary cells of this kind are commercially available (Clonetics/InVitrogen) and will expand as adherent cells in short-term tissue culture with specialized growth media. In addition, mammary epithelial carcinoma cells derived from breast cancer metastases are available from the American Type Tissue Culture Collection (ATCC). In order to better control for tumor to tumor variability, three different mammary epithelial carcinoma cell lines were studied: HCC-1 500, HCC-1 569, and HCC-1428. These lines were established from metastases in three separate patients and were purchased from ATCC as frozen stocks. The cell lines grew adherent to plastic, were expanded by routine tissue culture methods, and used experimentally.

Normal and cancerous mammary epithelial cells were harvested separately by brief incubation with trypsin/EDTA at 37 degrees Celsius. The cells were washed once in cold phosphate buffer solution (PBS) containing 1% FCS, counted, and used experimentally. The three separate mammary epithelial carcinoma cell lines were pooled in equal proportions for the experiments described below.

Normal mammary epithelial cells were stained with a fluorescein-conjugated monoclonal antibody to the HLA Class I MHC cell surface protein by incubating the cells with the appropriate, predetermined dilution of the mAb for 30 minutes at 4 degrees C. Despite the fact that mammary carcinomas are known to down-regulate Class I MHC expression, as a precaution, the normal cells were fixed in 1% paraformaldehyde to limit passive transfer to the carcinoma cells. The combined mammary carcinoma cells lines were also fixed in 1% paraformaldehyde and added to the normal mammary cell population. DRAQ5 (BioStatus, Ltd, Leicestershire, UK), a DNA binding dye that can be excited with a 488 nm laser and emits in the red waveband, was added to the sample prior to running on the ImageStream™ instrument. The labeling of normal mammary epithelial cells with anti-Class I MHC mAb enabled the normal cells to be identified in mixes of normal and carcinoma cells, thereby providing an objective "truth" to facilitate the identification of image features distinguishing normal epithelial cell from epithelial carcinoma cells.

Normal peripheral blood was obtained from AllCells (San Diego, Calif.). Whole blood was incubated with FITC conjugated anti-CD45 mAb, which is expressed at some level on all peripheral white blood cells. Red blood cells were then lysed by incubation of the whole blood in a Becton Dickinson FACSLyse™ for 3 minutes at room temperature. The cells were washed in PBS, counted and fixed with 1% paraformaldehyde. Mammary epithelial carcinoma cells were prepared as above, fixed in 1% paraformaldehyde and added to the peripheral blood cells. DRAQ5 was then added as a nuclear stain, and the cells were run on the ImageStream™ instrument.

Image files containing image data of the cell mixes described above (normal mammary epithelial cells mixed with mammary carcinoma cells, and normal peripheral blood cells mixed with mammary carcinoma cells) were analyzed using the IDEAS™ software package with the results described below.

After performing spectral compensation on the data file, an initial visual inspection was performed to compare normal mammary epithelial cells (positive for anti-HLA-FITC) to the carcinoma cells (unstained for anti-HLA-FITC). Representative images of normal cells are shown in FIG. 6, while representative images of carcinoma cells are shown in FIG. 7. In each Figure, each horizontal row includes four simultaneously acquired images of a single cell. Images in columns 61a and 71a correspond to blue laser side scatter images (i.e., dark field images), images in columns 61b and 71b correspond to green HLA-FITC fluorescence images, images in columns 61c and 71c correspond to bright field images, and images in columns 61d and 71d correspond to red nuclear fluorescence. As described above, the preferred imaging system is capable of simultaneously collecting six different types of images of a single cell (a dark field image, a bright field image, and four fluorescence images); in FIGS. 6 and 7, two of the fluorescence channels have not been utilized. It should be recognized that FIGS. 6 and 7 have been modified to facilitate their reproduction. As full-color images, the backgrounds of FIGS. 6 and 7 are black, images in columns 61a and 71a are blue, images in columns 61b and 71b are green, images in columns 61c and 71c are grayscale images on a gray background, and images in columns 61d and 71d are red.

When visually comparing full-color images of FIGS. 6 and 7, it is immediately apparent that images of normal mammary epithelial cells in column 61c (the green fluorescence channel) of FIG. 6 are vivid, while images of carcinoma cells in column 71c (the green fluorescence channel) of FIG. 7 can hardly be distinguished. It is also apparent that while none of the dark field images (columns 61a and 71a) are particularly intense, the dark field images (column 61a) of normal mammary epithelial cells in FIG. 6 are significantly more intense than are the dark field images (column 71a) of carcinoma cells in FIG. 7. Yet another qualitative observation that can be readily made is that the average intensity of the red fluorescence images (column 71d) of carcinoma cells in FIG. 7 is substantially greater than the average intensity of the red fluorescence images (column 61a) in FIG. 6. Further qualitative observations indicate that normal cells have higher heterogeneity, were generally larger, and had lower nuclear intensity. The subsequent analysis sought to quantitate these differences, as well as to discover additional parameters that might have discrimination capability. A screen capture of the corresponding IDEAS™ analysis is shown in FIG. 8A.

The analysis shown in FIG. 8A proceeded from a dot plot 81 in FIG. 8B. Single cells were first identified, based on dot plot 81, which was defined as bright field area versus aspect ratio. A gate (not separately shown) was drawn around the population containing putative single cells based on the criteria of the area being sufficiently large to exclude debris, and the aspect ratio being greater than −0.5, which eliminates doublets and clusters of cells. The veracity of the gating was tested by examining random cells both within and outside of the gate using the click-on-a-dot visualization functionality.

Figure 8C:
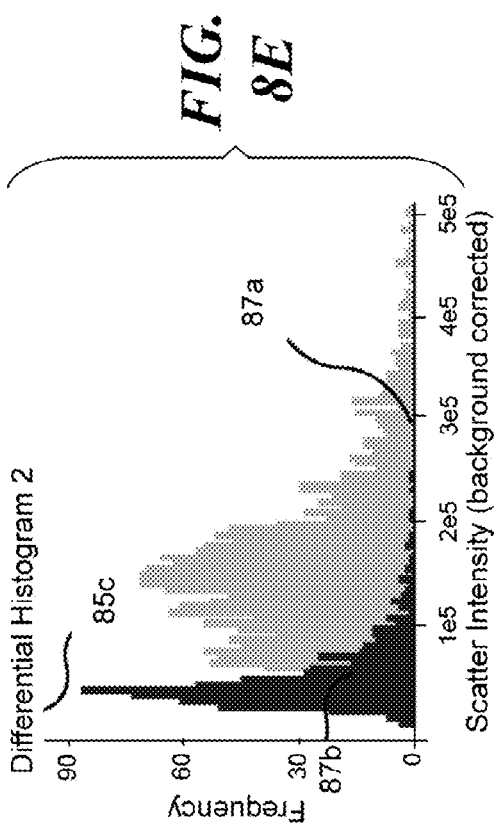
Figure 8D:
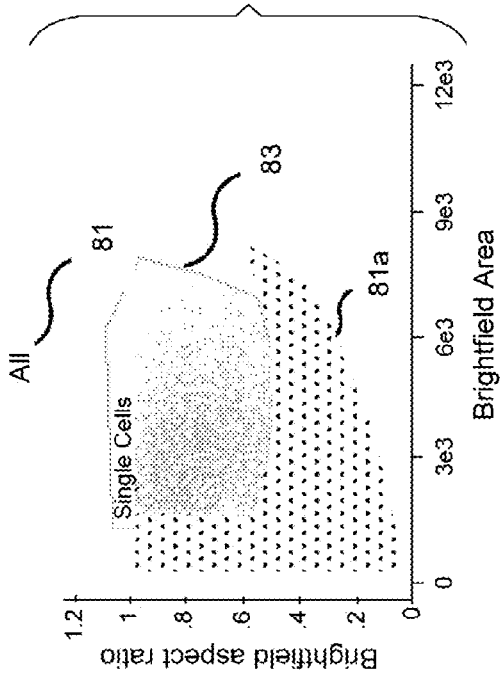
Figure 8E:
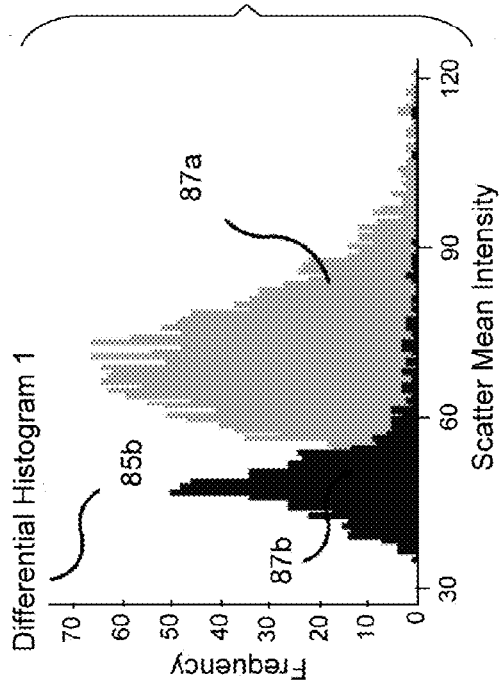
Figure 8F:
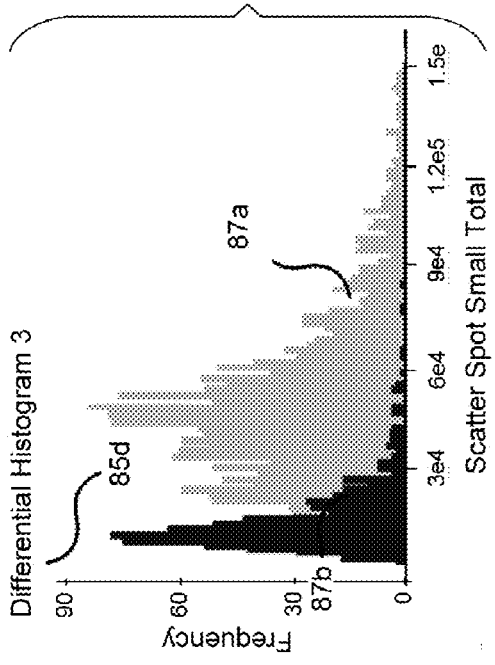
Figure 8G:
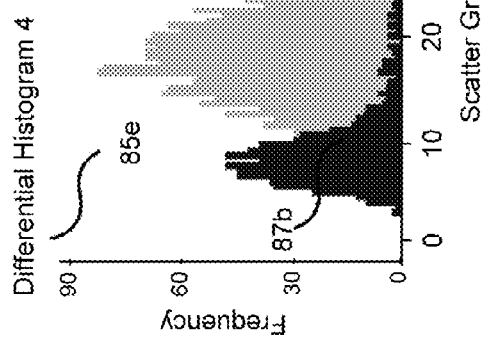
Figure 8H:
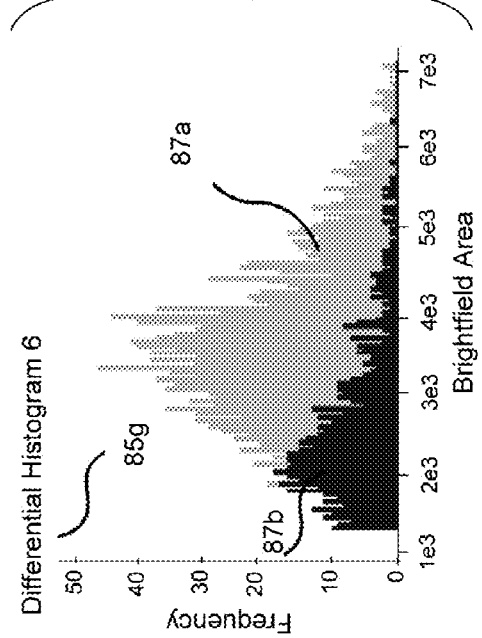
Figure 8I:
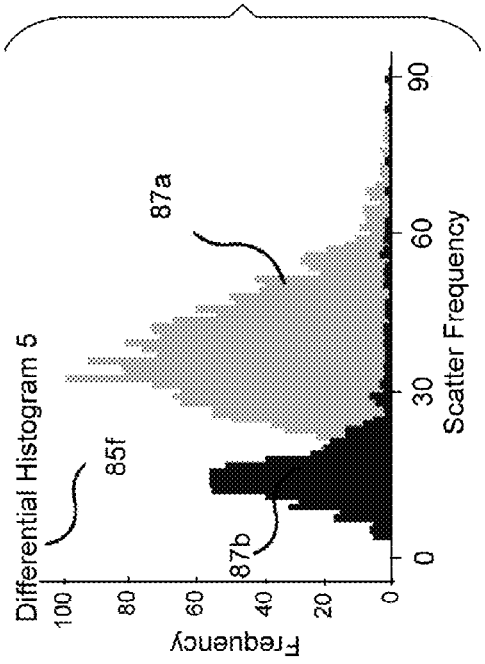
Figure 8J:
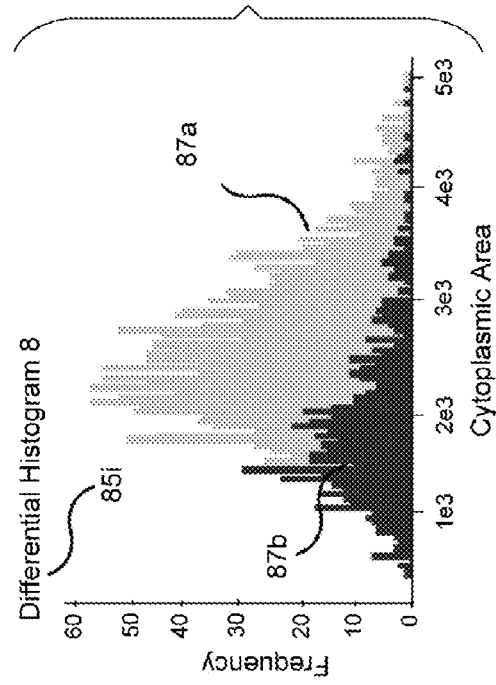
Figure 8K:
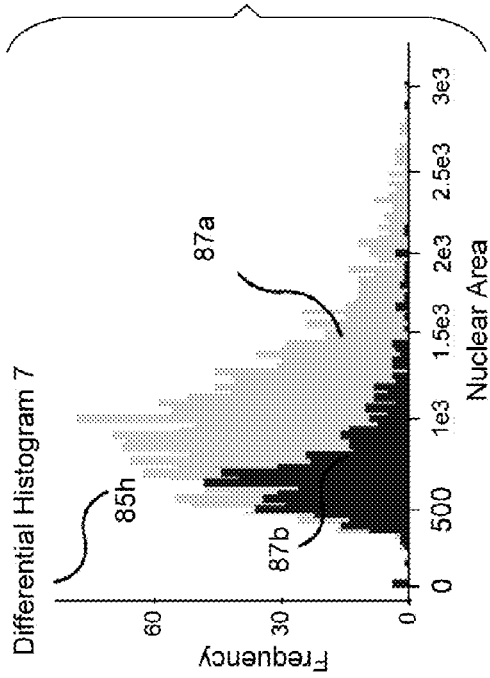
Figure 8L:
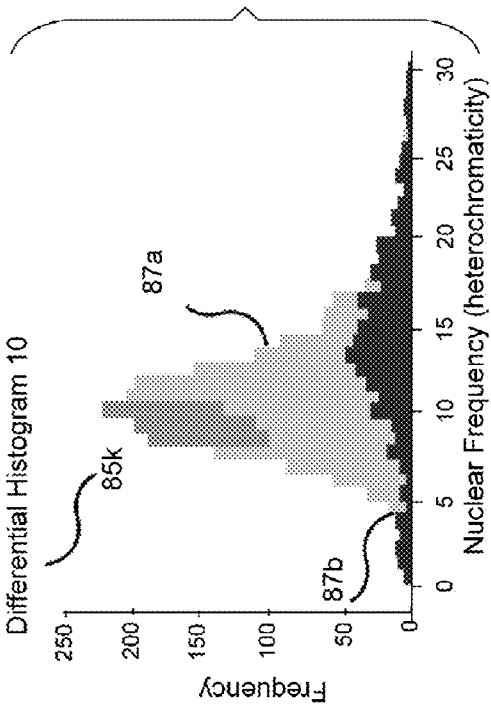
Figure 8M:
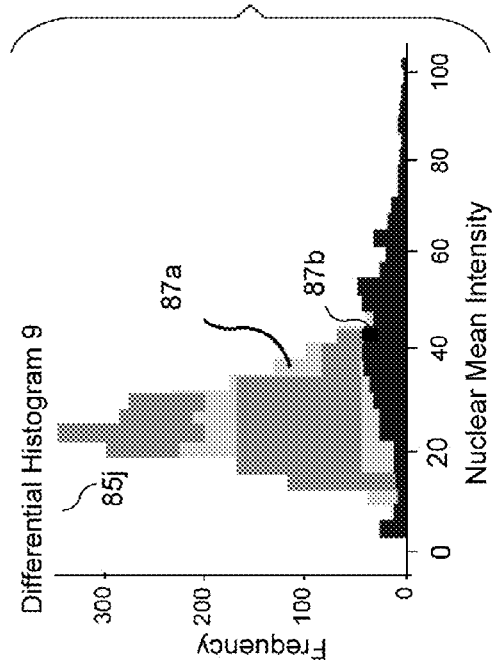

Next, the normal mammary cells were distinguished from the mammary carcinoma cells using the anti-HLA-FITC marker that was applied only to the normal cells. A solid yellow histogram 85a of FITC intensity was generated and is shown in FIG. 8C. A gate 83 was then drawn around the FITC positive (normal mammary epithelial cells) and FITC negative (mammary epithelial carcinoma cells), resulting in a subpopulation of 2031 normal cells, and a subpopulation of 611 carcinoma cells. These subpopulations were then used to identify image features that quantitatively discriminated between normal and cancerous cells, based on differential histograms. It should be recognized that FIG. 8A has been modified to facilitate its reproduction. As a full-color image, the background of each frame including a cell is black, and the background for each dot plot and histogram is black, to facilitate visualization of the cells and data. This modification resulted in the even distribution of dots 81a, even though such an even distribution was not present in the full color image.

The remaining ten histograms (i.e., histograms 85b-85k) shown in FIGS. 8D-8M are differential histograms of the normal cells 87a (shown as green in a full-color image) and carcinoma cells 87b (shown as red in a full-color image), with each histogram representing a different quantitative image feature. The ten discriminating image features fell into five distinct classes: scatter intensity, scatter texture, morphology, nuclear intensity, and nuclear texture. Differential histograms 85b, 85c, and 85d demonstrate the difference between the two populations using three different, but correlated, scatter intensity image features: "scatter mean intensity" (total intensity divided by cell area), "scatter intensity" (total intensity minus background), and "scatter spot small total" (total intensity of local maxima). Although all three scatter intensity image features provided good discrimination, "scatter mean intensity" (histogram 85b) was the most selective.

Differential histograms 85e and 85f quantitated scatter texture using either an intensity profile gradient metric ("scatter gradient RMS"; histogram 85e) or the variance of pixel intensities ("scatter frequency"; histogram 85o, which proved more selective.

Differential histograms 85g, 85h and 85i plotted the cellular area (bright field area, histogram 85g), nuclear area (from the DNA fluorescence imagery, histogram 85h), and cytoplasmic area (cellular/nuclear area, histogram 85i). The carcinoma cell lines were generally smaller in bright field area, confirming the qualitative observations from cell imagery. While the nuclear area of the carcinoma cell lines was proportionately smaller than that of the normal cells (e.g., the Nuclear/Cellular area ratio was not discriminatory), the cytoplasmic area was significantly lower in the carcinoma cells.

Finally, differential histograms 85j and 85k plotted the nuclear mean intensity (histogram 85j) and nuclear frequency (heterochromaticity, histogram 85k), respectively. As in the case of scatter, both of these image features provided some discriminatory power.

The multispectral/multimodal imagery collected by the ImageStream™ instrument and analyzed using the IDEAS™ software package in this engineered experiment revealed a number of significant differences in dark field scatter, morphology, and nuclear staining between normal epithelial and epithelial carcinoma cells. While it is well-recognized that cells adapted to tissue culture have undergone a selection process that may have altered their cellular characteristics, these data demonstrate that it is feasible to build an automated classifier that uses the morphometric and photometric image features identified and described above to separate normal from transformed epithelial cells, and possibly other cell types.

A further experimental investigation analyzed image data collected from a mixture of normal peripheral blood cells and mammary carcinoma cells. As shown in FIG. 5 (discussed above), cell classification of human peripheral blood can be achieved using a flow imaging system configured to simultaneously obtain a plurality of images of each cell, and using an automatic image analysis program (with the ImageStream™ instrument representing an exemplary imaging system, and the IDEAS™ software package representing an exemplary image analysis program). Using CD45 expression combined with an analysis of dark field light scatter properties, cells can be separated into five distinct populations based on the image data collected by the flow imaging system: lymphocytes, monocytes, neutrophils, eosinophils and basophils. This separation of human peripheral blood into distinct subpopulations is shown in greater detail in FIG. 9, which includes exemplary relative abundance data for the different subpopulations. The veracity of the classifications was determined by using population-specific monoclonal antibody markers and backgating marker-positive cells on the scatter vs. CD45 plot, as well as morphological analysis of the associated imagery. The x-axis of the graph in FIG. 9 corresponds to anti-CD45-FITC Intensity, while the y-axis corresponds to dark field scatter intensity.

In order to determine whether the techniques disclosed herein (utilizing the flow imaging instrument system described above, which is exemplified by the ImageStream™ instrument, and imaging analysis software, which is exemplified by the IDEAS™ software package) could discriminate epithelial carcinoma cells from normal PBMC, an artificial mixture of tumor cells and normal PBMC was produced as described above. The cell mixture was labeled with an anti-CD45-FITC mAb and a fluorescent DNA binding dye in order to differentiate PBMC subpopulations, generally as described above. A comparison of the scatter vs. CD45 bivariate plots for normal peripheral blood mononuclear cells and the PBMC sample spiked with the carcinoma cells is shown in FIGS. 10A and 10B. FIG. 10A graphically illustrates a distribution of normal peripheral blood mononuclear cells (PBMC) based on image data collected from a population of cells that does not include mammary carcinoma cells. FIG. 10B graphically illustrates a distribution of normal PBMC and mammary carcinoma cells based on image data collected from a population of cells that includes both cell types, illustrating how the distribution of the mammary carcinoma cells is distinguishable from the distribution of the normal PBMC cells. In this analysis, carcinoma cells 101a fall well outside of a normally defined PBMC population 101b, as confirmed by visual inspection of the outlier population.

As shown in FIGS. 11A and 11B, carcinoma cells 111a can also be discriminated from normal PBMC 111b using some of the morphometric and photometric image features identified in FIG. 8A (e.g., nuclear area, cytoplasmic area, scatter intensity, and scatter frequency). FIG. 11A graphically illustrates a distribution of normal PBMC and mammary carcinoma cells based on measured cytoplasmic area derived from image data collected from a population of cells that includes both cell types, illustrating how the distribution of cytoplasmic area of mammary carcinoma cells is distinguishable from the distribution of cytoplasmic area of the normal PBMC cells. FIG. 11B graphically illustrates a distribution of normal PBMC and mammary carcinoma cells based on measured scatter frequency derived from image data collected from a population of cells that includes both cell types, illustrating how the distribution of the scatter frequency of the mammary carcinoma cells is distinguishable from the distribution of the scatter frequency of the normal PBMC cells. Although these image features were initially identified for the purpose of discriminating between normal mammary and mammary carcinoma cells, they provide a high level of discrimination between mammary epithelial carcinoma cells and PBMC. Significantly, normal epithelial cells would be even more clearly differentiated from PBMC and distinct from the epithelial carcinoma cells using these parameters.

It should be recognized that FIGS. 10A, 10B, 11A, and 11B have been modified to facilitate their reproduction. As a full-color images, the background of each frame including a dot plot is black, to facilitate visualization of the cells and/or data, and dots representing PBMC cells and carcinoma cells are different colors.

The results noted above were verified by visual inspection of the segregated images (i.e., the images separated into subpopulations corresponding to carcinoma cells and healthy cells using one or more of the above identified photometric and/or morphometric parameters). Image gallery data were produced from the spiked PBMC data described above. FIG. 12 includes representative images from the carcinoma cell population, obtained using an overlay composite of bright field and DRAQ5 DNA fluorescence (red, with the image processing being performed by the image analysis software). FIG. 13 includes images of the five peripheral blood mononuclear cell populations defined using dark field scatter, CD45 (green), and DRAQ5 (red) for nuclear morphology. Note that the two Figures are at different size scales. It should be recognized that FIG. 12 has been modified to facilitate its reproduction. As a full-color image, the background of FIG. 12 is black, the background of each frame including a cell is brown/grey, and the nucleus of each is cell is red. FIG. 13 has been similarly modified to facilitate its reproduction. As a full-color image, the background of FIG. 13 is black, the periphery of each cell is green, and the nucleus of each is cell is red.

Significantly, the above studies demonstrate the feasibility of optically discriminating a subpopulation of normal epithelial cells from a subpopulation of transformed cells by analyzing multi-spectral/multimodal image data from a mixed population of such cells, where the image data are simultaneously collected. The above studies also demonstrate the feasibility of detecting epithelial carcinoma cells in blood by analyzing multi-spectral/multimodal image data from a mixed population of such cells, where the image data are simultaneously collected.

With respect to applying the concepts described herein to a specific disease condition concept, because of the relatively high operating speed of the exemplary imaging system (~100 cells/second or ~350,000 cells/hour), and because of the relatively large amount of image information collected for each cell (high resolution bright field image, dark field image, and four fluorescence images), it is believed that the concept disclosed herein is particularly suitable for the detection and monitoring of chronic lymphocytic leukemia.

In such an application, a 360 nm UV laser will be incorporated into the simultaneous multispectral/multimodal imaging system, and the optics of the imaging system will be optimized for diffraction-limited imaging performance in the 400-460 nm (DAPI emission) spectral band. The exemplary imaging system used in the empirical studies detailed above (i.e., the ImageStream™ instrument) employs a solid state, 200 mW, 488 nm laser for fluorescence excitation. While such a laser wavelength excites a broad range of fluorochromes, it is not optimal for cell cycle analysis due to its inability to excite DAPI, which binds stoichiometrically to DNA. In addition, the beam is configured to have a narrow width, which improves overall sensitivity in exchange for increased measurement variation from cell to cell. Feasibility studies employing propidium iodide as a DNA stain indicate that the imaging system employing the 488 nm laser can generate cell cycle histograms having G0/G1 peak coefficients of variation of ~5%.

In order to generate high resolution cell cycle histograms for the detection of changes in DNA content associated with CLL, the DAPI optimized 360 nm UV laser will instead be used. The beam will be configured to have a relatively wide illumination cross-section (~100 microns), so that under typical operating conditions, DAPI excitation consistency will be within 1% from cell to cell. Overall, cell cycle histogram CV is expected to be about 2-3%. In addition, the optics in the exemplary instrument used in the empirical studies discussed above are diffraction-limited from 460-750 nm, which does not cover the DAPI spectral emission band. Thus, such optics will be replaced with optics that are configured to achieve diffraction-limited imaging performance in the 400-460 nm spectral band, in order to measure detailed nuclear characteristics of diagnostic value, such as notched morphology and heterochromaticity.

Particularly for use with applying the concept disclosed herein for the detection of changes in DNA content associated with CLL, it would be desirable to provide image processing software incorporating additional masking algorithms and image features that define nuclear morphology in normal samples, beyond those described above.

The morphometric image feature set available in the exemplary image processing software discussed above does not include boundary contour image features that quantitate nuclear lobicity, number of invaginations, and similar parameters. Because such image features capture many of the qualitative observations of nuclear morphology traditionally used by hematopathologists, they would be of extremely high utility in the analysis of leukocytes. Incorporation of such algorithms and image features would enable improved automated classification of normal cells, precursors, and transformed cells.

The boundary contour masking algorithm and associated image features employed in the empirical studies discussed above improve cell classification between eosinophils, neutrophils, monocytes, basophils, and lymphocytes in about ⅓ of cells of each type, as a function of their orientation with respect to the imaging plane. Cells that are not in one of two preferred orientations (out of six possible orientations) do not benefit from the previously employed algorithm and image features. To improve the cell classification, the boundary contour algorithm and image features can be extended to consistently classify normal leukocytes, independent of their rotational orientation, which will lead to a first-pass classifier between normal and transformed cells, by increasing the statistical resolution between the expected locations of normal cell distributions, thereby improving the ability to flag abnormal cells that fall outside the expected positions. Such a classifier will also enable the image features to be characterized for the morphologic differences observed between normal and transformed lymphocytes, to further improve discrimination, using the techniques generally discussed above.

To configure the imaging analysis software for the detection of changes in DNA content associated with CLL, an automated classifier will be incorporated into the software package. The automated classifier will incorporate at least one or more of the following photometric and/or morphometric parameters: DNA content, nuclear morphology, heterochromaticity, N/C ratio, granularity, CD45 expression, and other parameters. As discussed above, the classifier will be configured to analyze image data corresponding to a population of blood cells, to classify the population into the following subpopulations: lymphocytes, monocytes, basophils, neutrophils, and eosinophils.

Automated differential analysis of PBMC based on multimodal imagery simultaneously collected from cells in flow will be performed using imaging systems consistent with those described above, and imaging processing software consistent with those described above. PBMC will be stained with FITC conjugated anti-CD45 and the DNA binding dye, DAPI. Peripheral blood leukocytes will be classified in a five-part differential analysis into lymphocytes, monocytes, basophils, neutrophils, and eosinophils, generally as indicated in FIGS. 5, 9, and 13.

Data sets from peripheral blood leukocytes from CLL patients will be acquired and analyzed, as discussed above. The classification scheme developed for normal peripheral blood leukocytes will be applied to these data sets, and the identification of CLL cells will be determined by comparison with normal profiles. Various classifiers will be evaluated to determine which segments CLL cells best exemplify, generally as described above with respect to the histograms of FIG. 8. Among these will be: cell size, nuclear size, nuclear to cytoplasmic ratio, nuclear contour, nuclear texture, and cytoplasmic granules. Results will be compared with standard blood films from CLL patient samples to determine the veracity of the technique.

In addition to the normal staining protocol utilizing anti-CD45 as a marker, peripheral blood leukocytes will be stained with monoclonal antibodies to CD5 and CD20, plus DAPI, before image data are collected. This approach will enable the identification of the CLL cells according to accepted flow cytometric criteria. In this way, morphologic criteria can be correlated with the immunophenotype.

Analyzing large (10,000 to 20,000 white blood cell) data sets from multiple CLL patients will facilitate the optimization and selection of photometric and morphometric image features that can be used classify blood cells by subpopulation (i.e., lymphocytes, monocytes, basophils, neutrophils, and eosinophils).

Morphological heterogeneity has been observed in CLL cells; however, an accurate objective appreciation of the degree of this has not been achieved due to the technical difficulty of preparing and assessing peripheral blood films from patients consistently. Acquisition of large data sets from CLL patients using the multimodal imaging systems discussed above will enable the objective analysis of the degree of morphological heterogeneity by the imaging processing software package. The classifier(s) developed above will be applied to these data sets, and morphological heterogeneity assessed by analyzing the degree to which the particular classifier (e.g., nuclear size, N/C ratio, etc.) applies across the large populations of CLL cells. Based on this analysis, the classifier that most accurately identifies the greatest percentage of CLL cells will be optimized, so that the entire population is included by the classifier.

As noted above, when applied to CLL, the techniques disclosed herein are not being used to separate a population of cells into a subpopulation corresponding to healthy cells, and a subpopulation corresponding to diseased cells. Instead, image data collected from a population of blood cells will be used to separate the population of blood cells into subpopulations based on blood cell type (i.e., lymphocytes, monocytes, basophils, neutrophils, and eosinophils). Because CLL is associated with an increase in the amount of lymphocytes present in the blood cell population (i.e., an increase in the lymphocytes subpopulation), detecting an increase in lymphocytes provides an indication of the existence of the disease condition (i.e., CLL). While the preferred method described herein involves separating the blood cell population into a plurality of different subpopulations, it should be recognized that a CLL detection technique could be implemented simply by separating the blood cell population into a lymphocyte subpopulation and a non-lymphocyte subpopulation. Using empirical data representing average lymphocyte subpopulations in healthy patients, detection of a higher-than-average lymphocyte subpopulation provides an indication of a CLL disease condition.

In addition to initially detecting the CLL disease condition, the imaging and analysis techniques discussed in detail above can be applied to follow patients with CLL longitudinally to determine their response to treatment, stability of the clinical response, and disease relapse. Changes in peripheral blood populations, including both normal and any residual CLL, can be followed and correlated with clinical outcome.

Exemplary Computing Environment

As noted above, an aspect of the present invention involves image analysis of a plurality of images simultaneously collected from members of the population of cells. Reference has been made to an exemplary image analysis software package. FIG. 14 and the following related discussion are intended to provide a brief, general description of a suitable computing environment for practicing the present invention, where the image processing required is implemented using a computing device generally like that shown in FIG. 14. Those skilled in the art will appreciate that the required image processing may be implemented by many different types of computing devices, including a laptop and other types of portable computers, multiprocessor systems, networked computers, mainframe computers, hand-held computers, personal data assistants (PDAs), and on other types of computing devices that include a processor and a memory for storing machine instructions, which when implemented by the processor, result in the execution of a plurality of functions.

An exemplary computing system 150 suitable for implementing the image processing required in the present invention includes a processing unit 154 that is functionally coupled to an input device 152, and an output device 162, e.g., a display. Processing unit 154 include a central processing unit (CPU 158) that executes machine instructions comprising an image processing/image analysis program for implementing the functions of the present invention (analyzing a plurality of images simultaneously collected for members of a population of objects to enable at least one characteristic exhibited by members of the population to be measured). In at least one embodiment, the machine instructions implement functions generally consistent with those described above, with reference to the flowchart of FIG. 3, as well as the exemplary screenshots. Those of ordinary skill in the art will recognize that processors or central processing units (CPUs) suitable for this purpose are available from Intel Corporation, AMD Corporation, Motorola Corporation, and from other sources.

Also included in processing unit 154 are a random access memory 156 (RAM) and non-volatile memory 160, which typically includes read only memory (ROM) and some form of memory storage, such as a hard drive, optical drive, etc. These memory devices are bi-directionally coupled to CPU 158. Such storage devices are well known in the art. Machine instructions and data are temporarily loaded into RAM 156 from non-volatile memory 160. Also stored in memory are the operating system software and ancillary software. While not separately shown, it should be understood that a power supply is required to provide the electrical power needed to energize computing system 150.

Input device 152 can be any device or mechanism that facilitates input into the operating environment, including, but not limited to, a mouse, a keyboard, a microphone, a modem, a pointing device, or other input devices. While not specifically shown in FIG. 14, it should be understood that computing system 150 is logically coupled to an imaging system such as that schematically illustrated in FIG. 1, so that the image data collected are available to computing system 150 to achieve the desired image processing. Of course, rather than logically coupling the computing system directly to the imaging system, data collected by the imaging system can simply be transferred to the computing system by means of many different data transfer devices, such as portable memory media, or via a network (wired or wireless). Output device 162 will most typically comprise a monitor or computer display designed for human visual perception of an output image.

Comparison of Two Cell Populations to Evaluate Patient Health

As discussed in detail above, image data for a plurality of images of individual cells that are acquired simultaneously can be used to detect a disease condition. Note that such an application of the present approach is based on identifying and/or quantifying differences between a first cell population and a second cell population, by analyzing the image data collected for each cell population. Generally, as described above, the image data can be analyzed to identify quantifiable photometric and morphometric differences between the first and second cell populations. The image data can also be used to identify a cell type present in one of the first and second cell populations, but not in the other of the first and second cell populations. Similarly, the image data can also be used to identify differences in the relative numbers of cell types in the first and second cell populations, to determine if there are more or less of a particular cell type in the first population of cells, as compared to the second population of cells (and vice versa). These techniques can provide diagnostic information about a patient from whom the cells are obtained, beyond simply determining if a specific disease condition exists.

For example, assume a patient provides a first sample of blood or bodily fluid taken on a first date, and image data from that first population of cells are generated as described above. Image data from a subsequent sample (i.e., a second population of cells) taken on a later date can be compared to the image data from the first population of cells to identify differences between those populations. it may be possible to correlate those differences to some phenomenon occurring between the collection of the first population of cells and the second population of cells. By way of example, such phenomena can include, but are not limited to, exposure to stress conditions (such an analysis will enable researchers to better understand cellular reactions to specific stress factors, such as heat, cold, exercise, mental stress, emotional stress, etc.), exposure to radiation (such an analysis will enable researchers to better understand cellular reactions to specific types of radiation), a change in diet (such an analysis will enable researchers to better understand cellular reactions to specific types of dietary changes), a change in lifestyle (such an analysis will enable researchers to better understand cellular reactions to specific types of lifestyle changes), a change in a patient's use of nutritional supplements (such an analysis will enable researchers to better understand cellular reactions to the use of specific nutritional supplements), types of dietary changes, and a change in a patient's use of medications (such an analysis will enable researchers to better understand cellular reactions to the use of specific medications). While some such phenomena may be related to a specific disease condition, other phenomena may more generally be related to a patient's health and/or well being.

In the example provided immediately above, the first and second population of cells were obtained from a person at different times. It should also be understood that the first and second population of cells can be obtained from a person at the same time, but then treated differently before being imaged as described above. For example, a single blood sample or bodily fluid sample can be acquired from a person, and that sample can be split into two fractions, one for the first population and the other fraction for the second population. Image data for the first fraction (the first population of cells) can then be acquired. The second fraction (the second population of cells) can be exposed to one of more phenomena, such as those noted above, and then imaged (note that the second fraction can be manipulated and/or exposed to some stimulus other than those specifically identified above). The image data from the first and second populations of cells can then be analyzed to determine how the cell populations differ as a result of changes in the second population caused by the phenomena, manipulation, or stimulation.

FIG. 15 is a flow chart 401 schematically illustrating exemplary steps that can be used to analyze two populations of cells based on images of the cell populations, in order to identify and/or quantify differences between the cell populations. In a particularly preferred exemplary embodiment, each cell population is obtained from a bodily fluid, such as blood. In a block 403, an imaging system, such as the exemplary imaging system described in detail above, is used to collect image data from a first population of biological cells. In a block 405, the imaging system is also used to collect image data from a second population of biological cells. As noted above, the first and second cell populations can be acquired at different times, or may be obtained from a single sample acquired at one time and the sample then split into two fractions. In a block 407, the image data from the two cell populations are computationally analyzed (using a processor, such as provided by a computing device or an application specific circuit, or other logic device) to identify differences between the cell populations. In at least some exemplary embodiments, the differences are quantified in terms of at least one photometric or morphometric image feature. In terms of the exemplary IDEAS™ software discussed above, the analysis can either look for specific changes identified by a user (such as a change in the relative abundance of cell types between the two populations), or the analysis can look for any and all differences that are identifiable based on the image data, and then rank those differences (in terms of morphological image features, photometric image features, and cell abundance) in order of their significance. Generally, as discussed above, the use of one or more fluorescent labels can facilitate the comparative analysis.

The high level steps of FIG. 15 can be used for many different types of investigations. The following provides a brief description of six different investigations that can be performed consistent with the exemplary steps of FIG. 15.

A first investigation analyzes image data from a first population of cells and a second population of cells to determine if any variation in a specific cell type present in both populations is indicative of a disease condition. This technique is described in significant detail above in the specification, in the context of using the first population to identify disease related image features, and looking for such image features in the second population.

A second investigation analyzes image data from a first population of cells and a second population of cells to determine if any variation exists for a specific cell type present in both populations, regardless of whether the difference is indicative of a disease condition. This technique is generally directed at acquiring the first and second cell populations from a person at different times, and determining if there is any difference between the same cell type in the first and second populations. If data are available regarding conditions experienced by the person during the time between acquiring the samples, then an attempt can be made to correlate the changes to such conditions. Even where no correlation can be found, any change identified may be indicative of the health of the person. For example, some cellular changes may suggest that the health of the patient has improved or declined, even if no specific disease condition is identified. Furthermore, even if no change in the first and second cell populations is identified, that finding may itself comprise valuable diagnostic data, either indicating that the health of the person has not appreciably changed, or if the person's health has changed, indicating that the specific cell type is likely not related to the change in health.

A third investigation analyzes image data from a first population of cells and a second population of cells to determine if there has been a change in the relative distributions of different types of cells present in both populations, where such a change can be indicative of a disease condition. This analysis will include determining if a specific cell type is present in the first cell population but not the second cell population, and vice versa, as well as determining how the relative percentage of cell types present in both the first and second cell populations has changed. This technique is described in significant detail above in the specification, in the context of using relative cell abundance to determine if a disease condition is indicated.

A fourth investigation also analyzes image data from a first population of cells and a second population of cells to determine if there has been a change in the relative abundance of different types of cells present in both populations, where such a change is not limited to indicating a specific disease condition, but may still be relevant to the health of the person from whom the first and second cell populations were obtained. Again, this analysis includes determining if a specific cell type is present in the first cell population but not the second cell population, and vice versa, as well as determining how the relative percentage of cell types present in both the first and second cell populations has changed. This technique is generally directed at acquiring the first and second cell populations from a person at different times, and determining if there are differences between the distributions of different cell types in the first and second populations. If data are available indicating conditions experienced by the person during the time between acquiring the samples, then an attempt can be made to correlate the changes to such conditions. Even where no correlation can be found, any changes identified may be indicative of the health of the person. For example, some cellular distribution changes may suggest that the health of the patient has improved or declined, even if no specific disease condition is identified. Furthermore, even if no change in the cellular distributions in the first and second cell populations is identified, that fact itself may comprise valuable diagnostic data, either indicating that the health of the person has not appreciably changed, or if the person's health has changed, indicating that the cellular distribution is likely not related to the change in health.

A fifth investigation analyzes image data from a first population of cells and a second population of cells to determine how the second population of cells responds to a stimulus not applied to the first population of cells, in order to detect a disease condition. In general, this technique is based on acquiring one sample from a person, and splitting that sample into two different fractions (the two different cell populations could be acquired from the person at different times; however, doing so will introduce an additional variable). The first population of cells serves as a control. A stimulus is applied to the second population of cells. The term "stimulus" should be broadly interpreted as something likely to induce a change in the second population of cells relative to the first population of cells. By way of example, such a stimulus can include, but is not limited to, exposing the second population to a change in temperature, exposing the second population to a reagent, exposing the second population to radiation, exposing the second population to a change in environmental conditions, and exposing the second population to a drug. In general, the first population of cells will not be exposed to the stimulus. It should be noted that the first population of cells may be manipulated in some fashion to enable changes between the population of cells to be more readily apparent, such as labeling the first population of cells.

A sixth investigation, similar to the fifth investigation discussed above, analyzes image data from a first population of cells and a second population of cells to determine how the second population of cells responds to a stimulus not applied to the first population of cells. The sixth investigation differs from the fifth in that a change detected may not be indicative of a specific disease condition, while still being relevant to the health of the person from whom the populations of cells were obtained. Furthermore, as generally discussed above, even where the comparison of the first population to the second population does not indicate any significant changes, that information may in itself be relevant to the health of the person.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

What is claimed is:

1. An imaging system configured to acquire and analyze image data separately collected from a first population of cells and a second population of cells, where the image data for each of the first and the second population of cells include a plurality of images of individual cells that are acquired simultaneously, to enable differences between the first population and the second population of cells to be quantified, comprising:
   (a) a collection lens disposed so that light traveling from an individual cell passes through the collection lens and travels along a collection path;
   (b) a light dispersing element disposed in the collection path so as to disperse the light that has passed through the collection lens into a plurality of light beams, thereby producing dispersed light;
   (c) an imaging lens disposed to focus the dispersed light, producing focused dispersed light;
   (d) a detector disposed to receive the focused dispersed light, such that the focused dispersed light incident on the detector simultaneously produces a plurality of images of the individual cell, the plurality of images comprising the image data, wherein the plurality of images includes at least one type of image selected from the group consisting of:
      (i) darkfield images;
      (ii) brightfield images; and
      (iii) fluorescent images; and
   (e) a processor configured to analyze the image data for the plurality of images collected from individual cells in the first and second population of cells, to quantify at least one difference between the first population of cells and the second population of cells.

2. The imaging system of claim 1, wherein the plurality of images comprises at least one of the following two types of images:
   (a) multispectral images; and
   (b) multimodal images.

3. The imaging system of claim 1, wherein the processor is further configured to quantify a difference between a relative abundance of cell types in the first and the second population of cells.

4. The imaging system of claim 1, wherein the processor is further configured to quantify a difference relating to a first type of cell present in the first population of cells and the first type of cell present in the second population of cells.

5. The imaging system of claim 1, wherein the processor is further configured to identify at least one morphometric image feature that differs between the first and the second population of cells.

6. The imaging system of claim 1, wherein the processor is further configured to identify at least one photometric image feature that differs between the first and second population of cells.

7. The imaging system of claim 1, wherein the processor is further configured to quantify the difference between the first and second population of cells in regard to a distribution of a molecule within the cells of each population of cells.

8. The imaging system of claim 1, wherein the processor is further configured to identify at least one cell type present in one of the first and the second population of cells, but not in the other of the first and the second population of cells.

9. The imaging system of claim 1, wherein the light dispersing element comprises a plurality of filters that separate the light that has passed through the collection lens into the dispersed light, the dispersed light comprising a plurality of light beams of different wavelengths or wavebands.

10. The imaging system of claim 9, wherein the imaging lens focuses each light beam of a specific wavelength on a different portion of the detector so that the plurality of images comprise different spectral images of each of the individual cells, and the spectral images are disposed in different portions of the detector.

11. The imaging system of claim 10, wherein the processor is further configured to detect one or more markers included in the individual cells, by analyzing one or more of the spectral images.

12. The imaging system of claim 1, further comprising a light source disposed to illuminate each of the individual cells to facilitate forming at least one of a bright field image, a darkfield image, or fluorescent images, for each of the individual cells.

13. An imaging system for collecting, processing and analyzing image data simultaneously collected for individual cells in each of a plurality of different populations of cells to identify differences between individual cells of the plurality of different population of cells, comprising:
   (a) a light source for illuminating individual cells of the plurality of different populations while there is relative motion between the individual cells and the imaging system, light from the individual cells traveling along a collection path and through at least one collection lens, producing collected light;
   (b) an optical dispersing component disposed to receive the collected light and to disperse it as a plurality of dispersed light beams having different spectral characteristics;
   (c) at least one imaging lens that is disposed to receive and focus the dispersed light beams along separate paths;
   (d) a detector disposed so that the dispersed beam are simultaneously focused on different portions of the detector as a plurality of images of one or more of the individual cells currently being processed by the imaging system, the detector producing output signals corresponding to each of the plurality of images; and (e) a processor for analyzing the output signals from the detector to determine any differences between the individual cells of the plurality of populations.

14. The imaging system of claim 13, wherein the processor analyzes the output signals to detect any difference between at least one of the following types of images of the individual cells that are included in the plurality of populations:

(a) darkfield images;
(b) brightfield images; and
(c) fluorescent images.

15. The imaging system of claim 13, wherein the processor determines differences between the individual cells in the plurality of populations based on detecting a relative abundance of one or more markers in the plurality of images of the individual cells, wherein the one or more markers are identified by the processor by analyzing the output signal from the detector in response to specific spectral images of the individual cells in which the markers are present.

16. The imaging system of claim 13, wherein the processor determines the difference between the plurality of different populations in regard to a number of cell types present in each of the plurality of different populations.

17. The imaging system of claim 13, wherein the processor identifies one or more differences in morphological characteristics of the individual cells present in the plurality of different populations.

18. The imaging system of claim 13, wherein the processor further determines a disease condition of the individual cells in at least one of the plurality of different populations based upon the differences between the individual cells of the plurality of different populations detected by the processor.

19. An imaging system configured to acquire and analyze image data separately collected from a first population of cells and a second population of cells, where the image data for each of the first and the second population of cells include a plurality of images of individual cells that are acquired simultaneously, to enable differences between the first population and the second population of cells to be quantified, comprising:

(a) a collection lens disposed so that light traveling from an individual cell passes through the collection lens and travels along a collection path;

(b) a light dispersing element disposed in the collection path so as to disperse the light that has passed through the collection lens into a plurality of light beams, thereby producing dispersed light;

(c) an imaging lens disposed to focus the dispersed light, producing focused dispersed light;

(d) a detector disposed to receive the focused dispersed light, such that the focused dispersed light incident on the detector simultaneously produces a plurality of images of the individual cell, the plurality of images comprising the image data; and (e) a processor configured to analyze the image data for the plurality of images collected from individual cells in the first and second population of cells, to quantify at least one difference between the first population of cells and the second population of cells, wherein the processor is further configured to determine a disease condition in one of the first population of cells and the second population of cells based upon the at least one difference between the first population of cells and the second population of cells.

\* \* \* \* \*